United States Patent
Osterroth et al.

(10) Patent No.: US 9,540,436 B2
(45) Date of Patent: *Jan. 10, 2017

(54) USE OF ANTIBODIES FOR DETECTION OF IL-10

(71) Applicant: Biotest AG, Dreieich (DE)

(72) Inventors: Frank Osterroth, Dietzenbach (DE); Christoph Uherek, Seligenstadt (DE); Christoph Bruecher, Eschborn (DE); Peter Röttgen, Ladenburg (DE); Benjamin Daelken, Frankfurt am Main (DE); André Engling, Bad Homburg (DE); Chantal Zuber, Frankfurt am Main (DE); Niklas Czeloth, Dreieich (DE)

(73) Assignee: BIOTEST AG, Dreieich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,133

(22) Filed: Jan. 7, 2015

(65) Prior Publication Data

US 2015/0218270 A1    Aug. 6, 2015

Related U.S. Application Data

(62) Division of application No. 13/512,712, filed as application No. PCT/EP2010/068569 on Nov. 30, 2010, now Pat. No. 8,956,607.

(30) Foreign Application Priority Data

Nov. 30, 2009   (GB) .................................. 0920933.9
Nov. 30, 2009   (GB) .................................. 0920940.4
Nov. 30, 2009   (GB) .................................. 0920942.0

(51) Int. Cl.
G01N 33/53   (2006.01)
C07K 16/24   (2006.01)
G01N 33/68   (2006.01)
A61K 39/00   (2006.01)

(52) U.S. Cl.
CPC ......... *C07K 16/244* (2013.01); *G01N 33/6869* (2013.01); *A61K 2039/505* (2013.01); *C07K 2299/00* (2013.01); *C07K 2317/14* (2013.01); *C07K 2317/24* (2013.01); *C07K 2317/34* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,585,089 | A | 12/1996 | Queen et al. |
| 5,776,451 | A | 7/1998 | Hsu et al. |
| 5,837,232 | A | 11/1998 | de Waal Malefyt et al. |
| 5,854,027 | A | 12/1998 | Steipe et al. |
| 6,407,213 | B1 | 6/2002 | Carter et al. |
| 8,647,622 | B2 | 2/2014 | Lee et al. |
| 8,852,871 | B2 | 10/2014 | Osterroth et al. |
| 8,956,607 | B2 | 2/2015 | Osterroth et al. |
| 2005/0101770 | A1 | 5/2005 | Presta |
| 2015/0064179 | A1 | 3/2015 | Osterroth et al. |

FOREIGN PATENT DOCUMENTS

| DE | 19529026 | 1/1997 |
| EP | 0541214 | 5/1993 |
| JP | 09-508286 A | 8/1997 |
| RU | 2326127 C2 | 3/2006 |
| WO | 2004/056312 A2 | 8/2004 |
| WO | 2005/047326 | 5/2005 |
| WO | WO 2009/032661 | 3/2009 |

OTHER PUBLICATIONS

Al-Janadi et al., (1996) J. of Clin. Immunol.; 16(4): 198-207.
Asadullah et al., (2003) Pharmacol. Rev. Jun; 55(2): 241-69.
"Biotest: Half Year Report as of Jun. 30, 2006." (2006).
Biotest Group Company Presentation: BT-063 A new treatment for SLE—Jun. 2008.
Biotext AG (2009) "Biotest AG: Clinical Development of BT-063 Started."
Capper et al., Clin. Exp. Immunol. Nov. 2004; 138(2): 348-56.
Carbonneil, C. et al., J. Immunol., 2004; 172: 7832-7840.
Carbonneil, C. et al., Int. Immunol., 2004; 16: 1037-1052.
Casali et al., (1987) Science. Apr. 3; 236(4797): 77-81.
Casset et al., "A peptide mimetic of an anti-CD4 monoclonal antibody by rational design", Biochem Biophys Res Comm. 2003; 307:198-205.
Chen et al., "Selection and analysis of an optimized anti-VEGF antibody: crystal structure of an affinity-matured Fab in complex with antigen", J Mol Biol. 1999; 293: 865-881.
Chun et al., J. Clin. Immunol. Sep. 2007; 27(5): 461-6.
Coleman, 1994. Research in Immunology, 145: 33-36.
de Waal Malefyt et al., (1991) J. Exp. Med. 174: 1209-1220.
Diaclone catalogue: IL-10 Antibody: B-N10 PE conjugated (Oct. 2008).
Hahn BH. Systemic Lupus Erythematosus. In: Kasper DL, Braunwald E, Fauci AS, Hauser SL, Longo DL, Jameson JL, editors. In: Harrison's Principles of Internal Medicine (16th edition). New York (US): McGraw-Hill; 2005. pp. 1960-1967.
Hashimoto et al., (2001) J. Immunol. 167(7): 3619-25.

(Continued)

*Primary Examiner* — Shulamith H Shafer
(74) *Attorney, Agent, or Firm* — Robin L. Teskin; LeClairRyan, A Professional Corporation

(57) ABSTRACT

Provided is a humanized or chimeric antibody or fragment thereof capable of binding to interleukin-10 (IL-10), wherein said antibody or fragment thereof: (i) binds to the same region of IL-10 as the IL-10 receptor α (IL-I10Ra) and is not capable of binding IL-10 when the IL-10 is bound to the IL-10 receptor; and (ii) binds to IL-10 in homodimeric form by binding a discontinuous epitope comprising residues of both monomers. Further provided are related products and methods involving the use of the antibody or fragment thereof.

14 Claims, 15 Drawing Sheets

(56) References Cited

OTHER PUBLICATIONS

Holm et al., "Functional mapping and single chain construction of the anti-cytokeratin 8 monoclonal antibody TS1", Mol Immunol. 2007; 44(6): 1075-1084.
Honegger and Plückthun (2001) J. Mol. Biol., 309: 657-670.
Honegger, A., "Aho's Amazing Atlas of Antibody Anatomy", www.bioc.uzh.ch/antibody. Mar. 19, 2008.
Howard et al., (1992) J. Clin. Immunol. 12(4): 239-47.
Huhn et al., (1996) Blood Jan. 15: 87(2): 699-705.
Isaacs et al., (2001) Arthritis Rheum. 44(9): 1998-2008.
Josephson et al., (2002) Structure 10: 981-987.
Josephson et al., (2000) J. Biol. Chem. 275(18): 13552-13557.
Liu and Jones (1998) Cytokine 10(2): 140-147.
Liu and Jones (1998) Cytokine 10(2): 148-153.
Liu et al., (2008) Immunological Reviews 222: 9-27.
Llorente et al., (1993) Eur. Cytokine Netw. Nov.-Dec.; 4(6): 421-7.
Llorente et al., (1995) J. Exp. Med. 181: 839-844.
Llorente et al., (2000) Arthritis & Rheumatism 43(8): 1790-1800.
MacCallum et al., "Antibody-antigen interactions: contact analysis and binding site topography", J Mol Biol. 1996 262: 732-745.
Midgley et al., (2009) Arthritis Rheum. 60(8): 2390-401.
Moreau et al., (1996) Brain 119 (Pt 1): 225-37.
Moreau et al., (2006) Bioinformatics 22(9): 1088-1095.
Paul, Fundamental Immunology, 3rd Edition, 1993, pp. 292-295, under the heading "Fv Structure and Diversity in Three Dimensions".
Park et al., Clin. Exp. Rheumatol. May-Jun. 1998; 16(3): 283-8.
Pletnev et al., (2005) BMC Structural Biology, Jun. 28; 5:10.
Ravirajan et al., (2004) Rheumatology 43: 442-447.
Reineke et al., (1998) Protein Science 7: 951-960.
Reineke et al., (1999) Nature Biotechnology 17(3): 271-275.
Robak & Robak (2009) Current Drug Targets; 10: 26-37.
Rudikoff et al., Proc. Natl. Acad. Sci. USA, 79(6): 1979-1983, Mar. 1982.
Rules Based Medicine: Mean Values for 78 Analytes Aug. 2008.
Rutella S. et al., 2002; Blood, 100(7): 2562-2571.
Sabat et al., (1996) Molecular Immunology 33(4): 1103-11.
Sanz and Lee (2010) Nat. Rev. Rheumatol. 6: 326-337.
Schultz "Biotest Autumn Conference for Journalists and Analysts", (2004).
Strand et al., (2007) Nat. Rev. Drug Discovery 6: 75-92.
Tucci et al., Clin. & Exp. Immunol. (2008); 154:247-254.
Vajdos et al., "Comprehensive functional maps of the antigen-binding site of an anti-ErbB2 antibody obtained with shotgun scanning mutagenesis", J Mol Biol. 2002; 320(2): 415-428.
Vargas-Rojas, MI et al., Lupus, 2008; 17(4): 289-294.
Waibler et al., J. Allergy Clin. Immunol. (2008) 122(5): 890-2.
Weiss L. et al., Blood, 2004; 104: 3249-3256.
Welfle et al., (2001) Journal of Molecular Recognition 14: 89-98.
Wing et al., (1996) J. Clin. Invest. 98(12): 2819-26.
Winkler et al., (1999) Blood 94(7): 2217-24.
Zdanov et al., (1995) Structure vol. 3, pp. 591-601.
English translation (Machine). DE 19529026 (A1)—Jan. 30, 1997.
Emilie D. "Interleukin 10 in disseminated lupus erythematosus," J Soc Biol. 2002;196(1):19-21.
Roskos L, et al. "The Clinical Pharmacology of Therapeutic Monoclonal Antibodies," Drug Development Research 2004 61:108-120.
Roskos L, et al. "Human Antiglobulin Responses," Measuring Immunity 2005, 172-86.
Tabrizi MA, et al. "Preclinical and clinical safety of monoclonal antibodies," Drug Discovery Today. Jul. 2007; 12(13-14):540-7.
A.A. Yarilin, "Foundations of Immunology: a textbook. Moscow, Medicine", 1999, 608 pages; p. 171, second paragraph, pp. 172-173.
Hwang et al., "Use of human germline genes in a CDR homology-based approach to antibody humanization", Methods, 2005, vol. 36, pp. 35-42.
Queen et al., "A humanized antibody that binds to the interleukin 2 receptor", Proc. Natl. Acad. Sci. USA, 1989, vol. 86, pp. 10029-10033.
Tsurushita et al., "Design of humanized antibodies: From anti-Tac to Zenapax", Methods, 2005, vol. 36, pp. 69-83.
Podchernyaeva, N.S. et al., "Systemic Lupus Erythematosus", Pediatric Pharmacology, 2006 vol. 3, N6; pp. 21-28 (English Translation).
Unknown, "Dictionary of Immunology (Menekigaku-Jiten), (2001), Second Edition, First Copy," entries for "H chain" ano "H chain variable region" on p. 92; "L chain" on p. 112; "L-chain variable region" on p. 113; "variable region" on p. 135; and "complementarity determining regions" on p. 384.

```
          10        20        30        40        50        60
          |         |         |         |         |         |
DVLMTQTPLSLPVSLGDQASISCRSSQNIVHSNGNTYLEWYLQKPGQSPKLLIYKVSNRF
                        LCDR1                          LCDR2
          70        80        90       100       110
          |         |         |         |         |
SGVPDRFSGSGSGTDFTLKITRLEAEDLGVYYCFQGSHVPWTFGGGTKLEIKRA
                                 LCDR3
```

FIGURE 1A

```
          10        20        30        40        50        60
          |         |         |         |         |         |
QVQLKQSGPGLLQPSQSLSISCTVSGFSLATYGVHWVRQSPGKGLEWLGVIWRGGSTDYS
                              HCDR1                    HCDR2
          70        80        90       100       110
          |         |         |         |         |
AAFMSRLSITKDNSKSQVFFKMNSLQADDTAIYFCAKQAYGHYMDYWGQGTSVTVS
                                  HCDR3
```

GATGTTTTGATGACCCAAACTCCACTCTCCCTGCCTGTCAGTCTTGGAGATCAAGCCTCC
ATCTCTTGCAGATCTAGTCAGAACATTGTACATAGTAATGGAAACACCTATTTAGAATGG
TACCTGCAGAAACCAGGCCAGTCTCCAAAGCTCCTGATCTACAAAGTTTCCAACCGATTT
TCTGGGGTCCCAGACAGGTTCAGTGGCAGTGGATCAGGGACAGATTTCACACTCAAGATC
ACCAGATTGGAGGCTGAGGATCTGGGAGTTTATTACTGCTTTCAAGGTTCACATGTTCCG
TGGACGTTCGGTGGAGGCACCAAGCTGGAAATCAAACGGGCC

CAGGTGCAGCTGAAGCAGTCAGGACCTGGCCTACTGCAGCCCTCACAGAGCCTGTCCATA
TCCTGCACAGTCTCTGGTTTCTCATTAGCTACCTATGGTGTACACTGGGTTCGCCAGTCT
CCAGGAAAGGGTCTGGAGTGGCTGGGAGTGATTTGGAGAGGTGGGAGCACAGACTACACT
GCAGCTTTCATGTCCAGACTGAGCATCACCAAGGACAACTCCAAGAGCCAAGTTTTCTTT
AAAATGAACAGTCTGCAAGCTGATGACACTGCCATTTACTTCTGTGCCAAACAGGCGTAT
CGTCACTACATGGACTACTGGGGTCAAGGAACCTCAGTCACCGTCTCC

FIGURE 2B

Humanized VL variants

```
mVL    DVLMTQTPLSLPVSLGDQASISC RSSQNIVHSNGNTYLE WYLQKPGQSPKLLIY KVSNRFS GVPDRFSGSGSGTDFTLKITRLEAEDLGVYYC FQGSHVPWT FGGGTKLEIK
A17    DVVMTQSPLSLPVTLGQPASISC RSSQSLVYSDGNTYLN WFQQRPGQSPRRLIY KVSNRDS GVPDRFSGSGSGTDFTLKISRVEAEDVGVYYC MQGTHWP..
JK1                                                                                                            ..WT FGQGTKVEIK hVL1   DVVMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL2   DVLMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL3   DVLMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL4   DVVMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGQGTKVEIK
hVL5   DVVMTQSPLSLPVTLGQPASISC RSSQNIVHSNGNTYLE WFQQRPGQSPRLLIY KVSNRFS GVPDRFSGSGSGTDFTLKISRVEAEDVGVYYC FQGSHVPWT FGQGTKVEIK
hVL6   DVVMTQSPLSLPVTLGQPASISC RSSQNIVHSNGNTYLE WFQQRPGQSPRRLIY KVSNRFS GVPDRFSGSGSGTDFTLKISRVEAEDVGVYYC FQGSHVPWT FGGGTKVEIK
hVL7   DVVMTQSPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGQGTKVEIK
hVL8   DVLMTQSPLSLPVTLGQPASISC RSSQNIVHSNGNTYLE WFQQRPGQSPRLLIY KVSNRFS GVPDRFSGSGSGTDFTLKISRVEAEDVGVYYC FQGSHVPWT FGGGTKVEIK
hVL9   DVLMTQSPLSLPVTLGQPASISC RSSQNIVHSNGNTYLE WYLQRPGQSPRLLIY KVSNRFS GVPDRFSGSGSGTDFTLKISRVEAEDVGVYYC FQGSHVPWT FGGGTKVEIK
hVL10  DVVMTQSPLSLPVTLGQPASISC RSSQNIVHSNGNTYLE WYLQRPGQSPRRLIY KVSNRFS GVPDRFSGSGSGTDFTLKISRVEAEDVGVYYC FQGSHVPWT FGGGTKVEIK
hVL11  DVVMTQSPLSLPVTLGQPASISC RSSQNIVHSNGNTYLE WYLQRPGQSPRRLIY KVSNRFS GVPDRFSGSGSGTDFTLKISRVEAEDVGVYYC FQGSHVPWT FGGGTKVEIK
hVL12  DVVMTQTPLSLPVTLGQPASISC RSSQNIVHSNGNTYLE WYLQRPGQSPRRLIY KVSNRFS GVPDRFSGSGSGTDFTLKISRVEAEDVGVYYC FQGSHVPWT FGQGTKVEIK
```

FIGURE 3

Humanized VH variants

```
mVH    QVQLKQSGPGLLQPSQSLSISCTVSGFSLA TYGVH WVRQSPGKGLEWLG VIWRGGSTDYSAAFMS RLSITKDNSKSQVFFKMNSLQADDTAIYFCAK QAYGHYMDY WGQGTSVTVSS 3-66   EVQLVESGGGLVQPGGSLRLSCAASGFTVS SNYMS WVRQAPGKGLEWVS VIYSGGSTYYADSVKG RFTISRDNSKNTLYLQMNSLRAEDTAVYYCAR

*O4

JH4                                                                                                                          ..YFDY WGQGTLVTVSS hVH1   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH2   EVQLVESGGGLVQPGGSLRLSCAASGFSFA TYGVH WVRQAPGKGLEWVS VIWRGGSTDYSAAFMS RFTISRDNSKNTLYLQMNSLRAEDTAVYYCAR QAYGHYMDY WGQGTLVTVSS
hVH3   EVQLVESGGGLVQPGGSLRLSCAASGFTFS TYGVH WVRQSPGKGLEWVS VIWRGGSTDYSAAFMS RFTISRDNSKNTLYLQMNSLRAEDTAVYYCAR QAYGHYMDY WGQGTLVTVSS
hVH4   EVQLVESGGGLVQPGGSLRLSCAASGFTFS TYGVH WVRQAPGKGLEWLG VIWRGGSTDYSAAFMS RFTISRDNSKNTLYLQMNSLRAEDTAVYYCAR QAYGHYMDY WGQGTLVTVSS
hVH5   EVQLVESGGGLVQPGGSLRLSCAASGFTFS TYGVH WVRQAPGKGLEWVS VIWRGGSTDYSAAFMS RLTISRDNSKNTLYLQMNSLRAEDTAVYYCAR QAYGHYMDY WGQGTLVTVSS
hVH6   EVQLVESGGGLVQPGGSLRLSCAASGFTFS TYGVH WVRQAPGKGLEWVS VIWRGGSTDYSAAFMS RFTISKDNSKNTLYLQMNSLRAEDTAVYYCAR QAYGHYMDY WGQGTLVTVSS
hVH7   EVQLVESGGGLVQPGGSLRLSCAASGFTFS TYGVH WVRQAPGKGLEWVS VIWRGGSTDYSAAFMS RFTISRDNSKNTVYLQMNSLRAEDTAVYYCAR QAYGHYMDY WGQGTLVTVSS
hVH8   EVQLVESGGGLVQPGGSLRLSCAASGFTFS TYGVH WVRQAPGKGLEWVS VIWRGGSTDYSAAFMS RFTISRDNSKNTLYFQMNSLRAEDTAVYYCAR QAYGHYMDY WGQGTLVTVSS
hVH9   EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYFCAK QAYGHYMDY WGQGTLVTVSS
hVH10  EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAK QAYGHYMDY WGQGTLVTVSS
hVH11  EVQLVESGGGLVQPGGSLRLSCAASGFTFS TYGVH WVRQAPGKGLEWVS VIWRGGSTDYSAAFMS RFTISRDNSKNTLYLQMNSLRAEDTAVYYCAR QAYGHYMDY WGQGTSVTVSS
hVH12  EVQLVESGGGLVQPGGSLRLSCAASGFTFS TYGVH WVRQAPGKGLEWLG VIWRGGSTDYSAAFMS RLTISRDNSKNTLYLQMNSLRAEDTAVYYCAR QAYGHYMDY WGQGTLVTVSS
```

FIGURE 3 (continued)

```
hVH13 EVQLVESGGGLVQPGGSLRLSCAASGFTFS TYGVH WVRQAPGKGLEWVS VIWRGGSTDYSAAFMS RFTISRDNSKNTVYFQMNSLRAEDTAVYYCAR QAYGHYMDY WGQGTLVTVSS
hVH14 EVQLVESGGGLVQPGGSLRLSCAASGFSFA TYGVH WVRQSPGKGLEWVS VIWRGGSTDYSAAFMS RFTISRDNSKNTLYLQMNSLRAEDTAVYFCAK QAYGHYMDY WGQGTLVTVSS
hVH15 EVQLVESGGGLVQPGGSLRLSCAASGFTFS TYGVH WVRQSPGKGLEWLG VIWRGGSTDYSAAFMS RFTISRDNSKNTLYLQMNSLRAEDTAVYFCAK QAYGHYMDY WGQGTSVTVSS
hVH16 EVQLVESGGGLVQPGGSLRLSCAASGFTFS TYGVH WVRQAPGKGLEWVS VIWRGGSTDYSAAFMS RFTISRDNSKNTLYFQMNSLRAEDTAVYFCAK QAYGHYMDY WGQGTLVTVSS
hVH17 EVQLVESGGGLVQPGGSLRLSCAASGFTFS TYGVH WVRQSPGKGLEWLG VIWRGGSTDYSAAFMS RFTISRDNSKNTLYLQMNSLRAEDTAVYYCAK QAYGHYMDY WGQGTSVTVSS
hVH18 EVQLVESGGGLVQPGGSLRLSCAASGFSFA TYGVH WVRQAPGKGLEWLG VIWRGGSTDYSAAFMS RLTISKDNSKNTLYLQMNSLRAEDTAVYYCAR QAYGHYMDY WGQGTLVTVSS
hVH19 EVQLVESGGGLVQPGGSLRLSCAASGFTFS TYGVH WVRQSPGKGLEWLG VIWRGGSTDYSAAFMS RLTISKDNSKNTVYFQMNSLRAEDTAVYFCAK QAYGHYMDY WGQGTSVTVSS
hVH20 EVQLVESGGGLVQPGGSLRLSCAASGFSFA TYGVH WVRQSPGKGLEWLG VIWRGGSTDYSAAFMS RLTISKDNSKNTVYFQMNSLRAEDTAVYFCAK QAYGHYMDY WGQGTSVTVSS
hVH21 EVQLVESGGGLVQPGGSLRLSCAASGFSFA TYGVH WVRQAPGKGLEWLG VIWRGGSTDYSAAFMS RLTISKDNSKNTVYFQMNSLRAEDTAVYFCAK QAYGHYMDY WGQGTSVTVSS
hVH22 EVQLVESGGGLVQPGGSLRLSCAASGFSFA TYGVH WVRQSPGKGLEWVS VIWRGGSTDYSAAFMS RLTISKDNSKNTVYFQMNSLRAEDTAVYFCAK QAYGHYMDY WGQGTSVTVSS
hVH23 EVQLVESGGGLVQPGGSLRLSCAASGFSFA TYGVH WVRQSPGKGLEWLG VIWRGGSTDYSAAFMS RFTISRDNSKNTVYFQMNSLRAEDTAVYFCAK QAYGHYMDY WGQGTSVTVSS
hVH24 EVQLVESGGGLVQPGGSLRLSCAASGFSFA TYGVH WVRQSPGKGLEWLG VIWRGGSTDYSAAFMS RLTISKDNSKNTVYFQMNSLRAEDTAVYFCAK QAYGHYMDY WGQGTSVTVSS
hVH25 EVQLVESGGGLVQPGGSLRLSCAASGFSFA TYGVH WVRQSPGKGLEWLG VIWRGGSTDYSAAFMS RLTISKDNSKNTLYFQMNSLRAEDTAVYFCAK QAYGHYMDY WGQGTSVTVSS
hVH26 EVQLVESGGGLVQPGGSLRLSCAASGFSFA TYGVH WVRQSPGKGLEWLG VIWRGGSTDYSAAFMS RLTISKDNSKNTVYLQMNSLRAEDTAVYFCAK QAYGHYMDY WGQGTSVTVSS
hVH27 EVQLVESGGGLVQPGGSLRLSCAASGFSFA TYGVH WVRQSPGKGLEWLG VIWRGGSTDYSAAFMS RLTISKDNSKNTVYFQMNSLRAEDTAVYYCAK QAYGHYMDY WGQGTSVTVSS
hVH28 EVQLVESGGGLVQPGGSLRLSCAASGFSFA TYGVH WVRQSPGKGLEWLG VIWRGGSTDYSAAFMS RLTISKDNSKNTVYFQMNSLRAEDTAVYYCAR QAYGHYMDY WGQGTSVTVSS
hVH29 EVQLVESGGGLVQPGGSLRLSCAASGFSFA TYGVH WVRQSPGKGLEWLG VIWRGGSTDYSAAFMS RLTISKDNSKNTVYFQMNSLRAEDTAVYFCAK QAYGHYMDY WGQGTLVTVSS
```

Figure 3 (Continued)

USE OF ANTIBODIES FOR DETECTION OF IL-10

CROSS REFERENCE TO RELATED APPLICATIONS

This application is a divisional of U.S. application Ser. No. 13/512,712 filed Sep. 5, 2012, pending, which is a 371 of PCT/EP2010/068569 filed Nov. 30, 2010, which claims priority to G.B. Application No. 0920933.9, filed Nov. 30, 2009, G.B. Application No. 0920940.4, filed Nov. 30, 2009, and G.B. Application No. 0920942.0, filed Nov. 30, 2009, all of which are incorporated by reference in their entireties.

SEQUENCE LISTING

The sequence listing in the file named "43297o1402.txt" having a size of 60,284 bytes that was created Jan. 7, 2015 is hereby incorporated by reference in its entirety.

FIELD OF THE INVENTION

The present invention is concerned with interleukin-10 (IL-10) and IL-10 specific agents. In particular, the present invention involves humanized IL-10 antibodies and their uses. The invention further envisages a method of treatment of systemic lupus erythematosus (SLE).

BACKGROUND TO THE INVENTION

Systemic lupus erythematosus (SLE) is regarded as an autoimmune disease, in which abnormal hyperactivity of B lymphocytes and massive abnormal production of immunoglobulin gamma (IgG) auto-antibodies plays a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: Harrison's Principles of Internal Medicine (16th edition). New York (US): McGraw-Hill; 2005. pp. 1960-1967).

SLE is characterized by diverse manifestations. In the course of the disease a total of 95% of patients complain of musculoskeletal disease, 80% show cutaneous lesions, 85% haematological disease, 60% neurological disorders, 60% cardiopulmonary disease, 30% to 50% renal disease, 40% gastrointestinal disease, 15% thrombosis and 15% ocular disease. The vast majority of the patients (95%) also suffer from systemic symptoms such as fatigue, malaise, fever, anorexia, and weight loss, which are present most of the time. Most patients experience disease periods of flares alternating with remissions. Permanent remissions (absence of symptoms with no treatment) are very rare. More than 50 years ago most patients diagnosed with SLE lived less than 5 years. Nowadays, 10 year survival is over 90%, mainly based on earlier diagnosis, symptomatic anti-inflammatory and immune-suppressive treatment. The common cause of death is infection as a result of immune-suppression (Hahn 2005).

Antimalarial, anti-inflammatory and immunosuppressive drugs have routinely been used in the treatment of SLE. Non-steroidal anti-inflammatories have been supplemented with corticosteroids when the symptoms become difficult to control. Further, active SLE, with major organ involvement, requires aggressive therapy with cyclophosphamide.

Up to now, there has been no causative treatment available to cure SLE and/or improve patients' quality of life on a long term basis. However, recent advances in antibody technology and the further identification of factors underlying this autoimmune disease have opened up the possibility of using monoclonal antibodies as a treatment option. In particular, a favourable approach to treat SLE would be a specific treatment interacting or correcting the pathological immune response resulting in the massive overproduction of polyclonal auto-antibodies. Since the pathogenesis of SLE primarily involves dysregulated B cells, monoclonal antibodies capable of targeting B-cells are of special interest. As noted by Robak and Robak (Current Drug Targets, 2009, No. 10, pages 26-37) potential B-cell surface antigen targets are CD19, CD20, CD21 and CD22. Further, IL-10, IL-Ira, IL-12 (Capper et al., Clin. Exp. Immunol. 2004 November; 138 (2):348-56), and IL-6 (Chun et al., J. Clin. Immunol. 2007 September; 27(5):461-6) are important cytokines in regulating immune response and are especially raised during flares in SLE patients. Plasma levels of IL-10 and auto-antibodies against double-stranded DNA (dsDNA) often mirror disease activity in patients with SLE. Raised IL-10 levels correlated with disease activity in SLE patients (Park et al., Clin. Exp. Rheumatol. 1998 May-June; 16(3):283-8). However, IL-10 is a cytokine with pleiotropic effects on the immune system and is also known to be involved in reducing proinflammatory responses.

Clinical trials with monoclonal antibodies have been conducted in SLE patients. In particular, several trials have involved the antibody Rituximab, a chimeric mouse anti-CD20 monoclonal antibody used for the treatment of non-Hodgkin's lymphoma. As noted by Robak and Robak (2009), the results of these trials show high activity of this antibody in SLE patients, and several new antibodies targeting CD20 have been developed; Ofatumumab, IMMU-106 and GA-101. Further clinical trials reporting activity of monoclonal antibodies in SLE have been completed with the anti-CD22 antibody, Epratuzumab, the anti-TNFα antibody, Infliximab, the anti-IL-10 antibody, B-N10 (Llorente et al., Arthritis Rheum. 2000 August; 43(8):1790-800), the anti-CD40L antibodies, IDEC 131 and BG 9588, the BLYS inhibitor, Belimumab, the anti-IL6 receptor antibody, Toclimumab, and the anti-C5 antibody Eculizumab.

It is the aim of the present invention to provide further agents, and in particular antibodies, having utility in this area.

Accordingly in a first aspect the present invention provides a humanized or chimeric antibody or fragment thereof capable of binding to interleukin-10 (IL-10), wherein said antibody or fragment thereof: (i) binds to the same region of IL-10 as the IL-10 receptor α (IL-10Rα) and is not capable of binding IL-10 when the IL-10 is bound to the IL-10 receptor; and (ii) binds to IL-10 in homodimeric form by binding a discontinuous epitope comprising residues of both monomers.

The present inventors have found that the antibodies of the present invention have a particularly advantageous mode of binding, such that they are suitable for treating medical conditions that are mediated by an elevated level or activity of IL-10, and in particular autoimmune diseases.

Specifically, the antibodies and fragments thereof of the present invention are not capable of triggering an ADCC or CDC response, since they are not able to bind to the IL-10 once it has bound to the IL-10Rα. This is a particularly advantageous mode of binding because, as a result, the antibodies of the present invention are not able to bind to cells on which IL-10 is bound to a receptor, and therefore cannot induce an ADCC or CDC response. In this way the impact of the antibody on other parts of the immune system is controlled. Still further, the antibodies and fragments thereof of the present invention are able to bind to the IL-10 homodimer with much greater affinity than to the IL-10 monomer. As such the antibody binds preferentially to the functionally active form of IL-10 rather than to the monomer or degradation products. This is particularly advantageous because it reduces the amount of IL-10 antibody required to produce a neutralizing effect and reduces the risk of side effects via non-specific binding to non-active molecules.

In a second aspect the present invention provides a humanized or chimeric antibody or fragment thereof capable of binding to interleukin-10 (IL-10), wherein said antibody or fragment thereof binds to the same region of IL-10 as the IL-10 receptor (IL-10Rα) and is not capable of binding IL-10 when the IL-10 is bound to the IL-10 receptor.

In a third aspect the present invention provides a humanized or chimeric antibody or fragment thereof that is capable of binding to interleukin-10 (IL-10) in homodimeric form, wherein said antibody or fragment thereof binds to a discontinuous epitope comprising residues of both monomers.

In a fourth aspect the present invention provides a humanized or chimeric antibody or fragment thereof according to claim 1 wherein the antibody or fragment thereof comprises amino acid sequences at least 80% identical to those of CDR 1, CDR 2 and CDR3 of the murine antibody B-N10 variable light chain and/or comprises amino acid sequences at least 80% identical to those of CDR 1, CDR 2 and CDR3 of the murine antibody B-N10 variable heavy chain.

In a fifth aspect the present invention provides a humanized or chimeric antibody or fragment thereof capable of binding to interleukin-10 (IL-10), wherein said antibody or fragment thereof does not induce antibody-dependent cell-mediated cytotoxicity and/or complement-dependent cytotoxicity.

In a sixth aspect the present invention provides a humanized or chimeric antibody or fragment thereof capable of binding to interleukin-10 (IL-10), wherein said antibody or fragment thereof is capable of preventing IL-10 signaling through the IL-10α receptor.

In a seventh aspect the present invention provides a humanized or chimeric antibody or fragment thereof capable of binding to interleukin-10 (IL-10), wherein said antibody or fragment thereof is not capable of binding to IL-1 OR expressing cells.

The invention will be illustrated by way of example only, with reference to the following Figures, in which:

FIG. 1A shows the amino acid sequence of the light chain variable region of the murine B-N10 antibody (SEQ ID No: 2). The hypervariable complementarity-determining regions (CDRs) are underlined (wherein LCDR1 is SEQ ID No: 4; LCDR2 is SEQ ID No: 5; and LCDR3 is SEQ ID No:6).

FIG. 1B shows the amino acid sequence of the heavy chain variable region of the murine B-N10 antibody (SEQ ID No: 3). The hypervariable complementarity-determining regions (CDRs) are underlined (wherein HCDR1 is SEQ ID No: 7; HCDR2 is SEQ ID No: 8; and HCDR3 is SEQ ID No:9).

FIG. 2A shows the nucleotide sequence encoding the light chain variable region of the murine B-N10 antibody (SEQ ID No: 10).

FIG. 2B shows the nucleotide sequence encoding the heavy chain variable region of the murine B-N10 antibody (SEQ ID No: 11).

FIG. 3 shows the amino acid sequence of the murine B-N10 light and heavy chain variable regions (SEQ ID Nos: 12 and 13, respectively) together with the sequences taken from A17 (SEQ ID No: 14), JK1 (SEQ ID No: 15), 3–66+04 (SEQ ID No: 16) and JH4 (SEQ ID No: 17) and the variable regions hVL1 to hVL12 (SEQ ID Nos: 18 to 29) and the variable regions hVH1 to hVH29 (SEQ Id Nos: 30 to 58) generated during the humanization of the murine B-N10 antibody.

Figure 4:
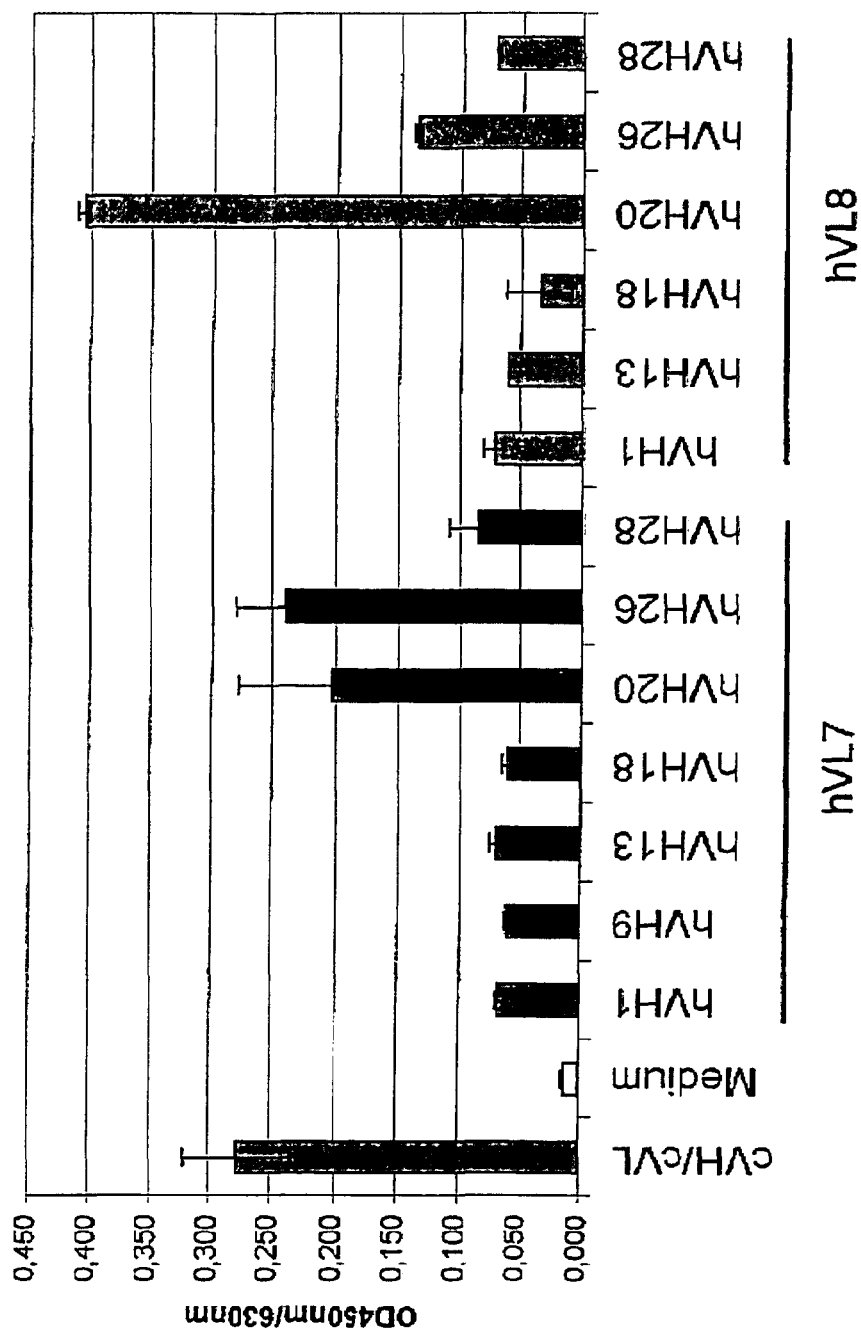

FIG. 4 provides a comparison of the antigen binding properties of the humanized antibody variants in comparison to a chimeric cB-N10 antibody using the hIL-10 antigen ELISA.

Figure 5:
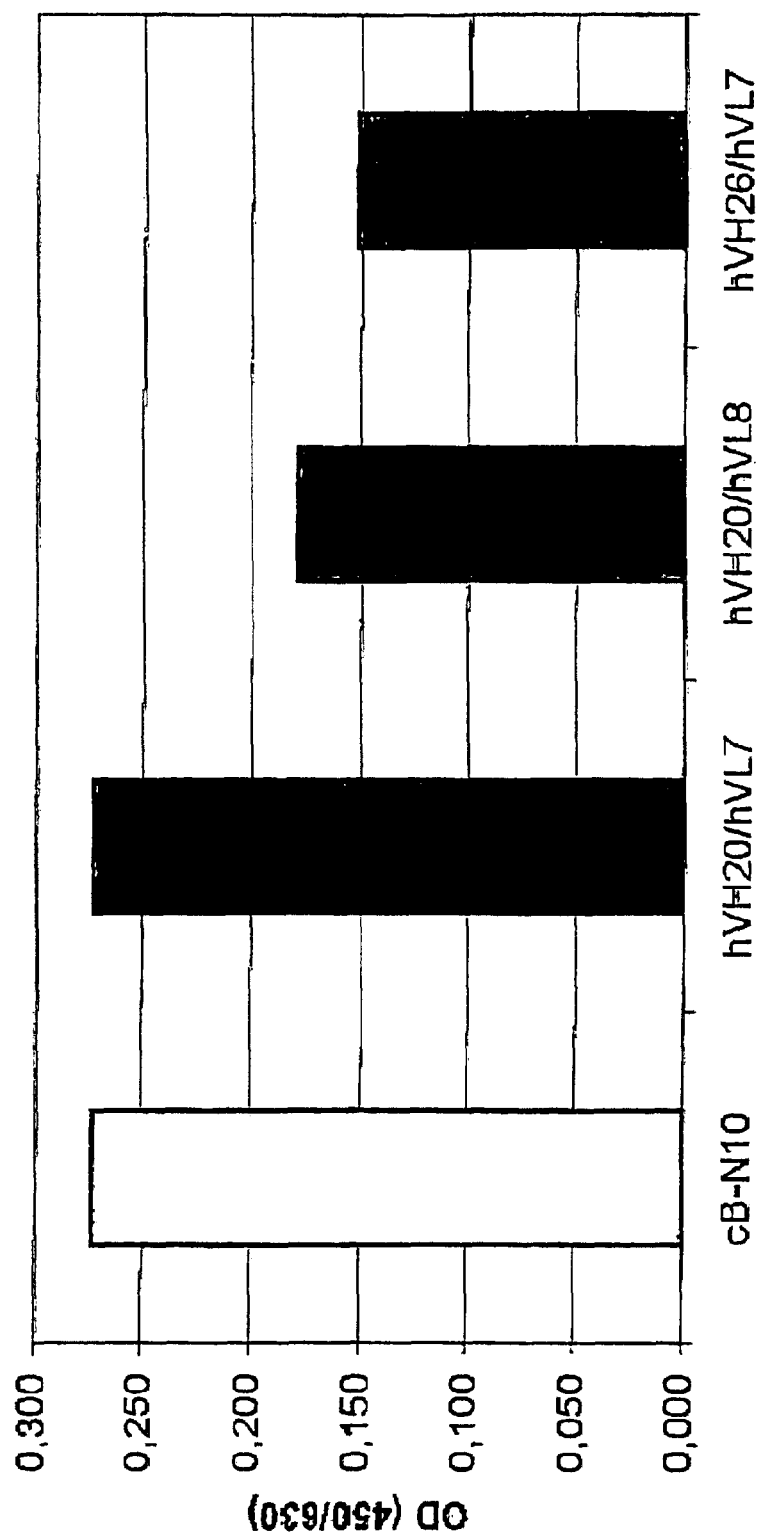

FIG. 5 provides the result of the determination of the binding properties of the three humanized variants, hVH20/hVL7, hVH20/hVL8 and hVH26/hVL7, in comparison to the chimeric B-N10 antibody using purified antibody preparations.

Figure 6:
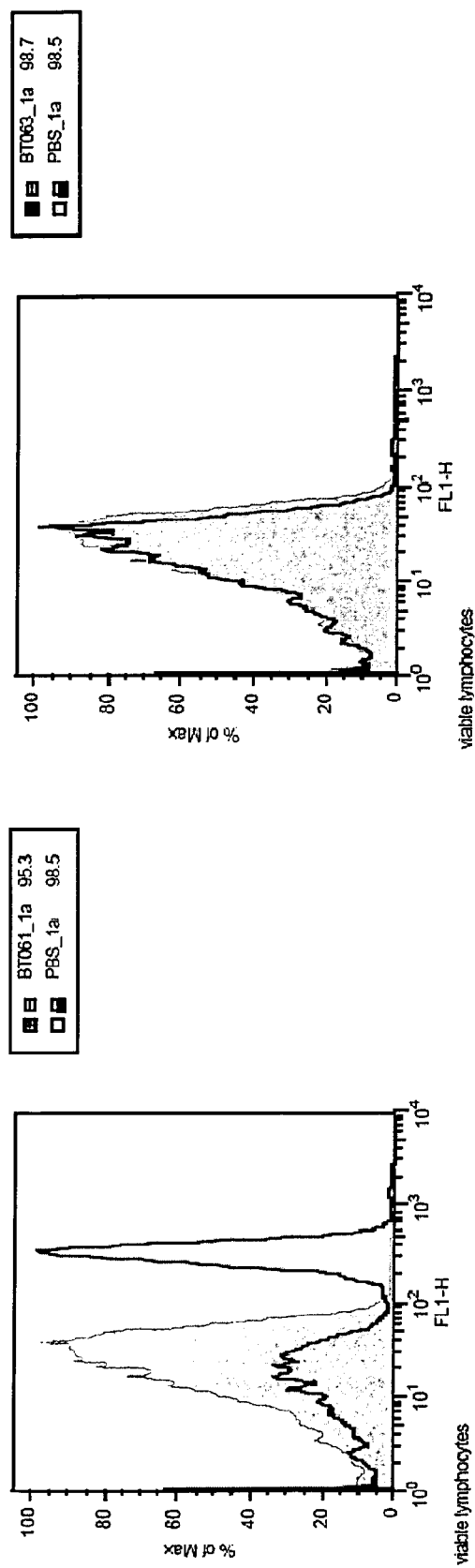

FIG. 6 shows the staining of lymphocytes with labeled BT061 and BT-063.

Figure 7:
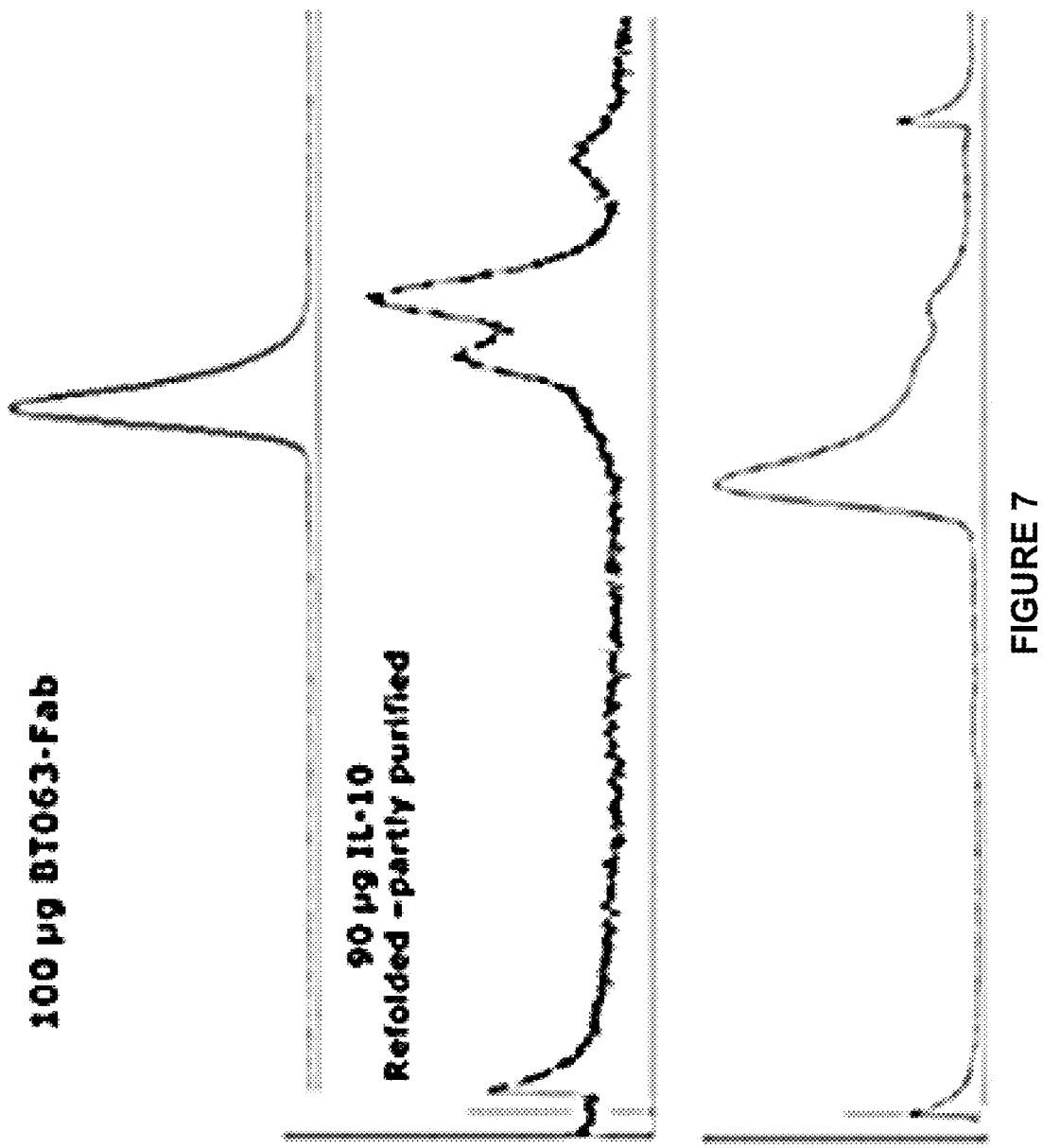

FIG. 7 shows size exclusion chromatography of BT-063 Fab (upper row), IL-10 monomer and dimer (middle row) and complex of IL-10 dimer and BT-063 Fab (lower row).

Figure 8:

FIG. 8 shows the overall structure of the Fab fragment of BT-063 binding IL-10. IL-10 and the Fab fragment are shown as a ribbon representation.

Figure 9:
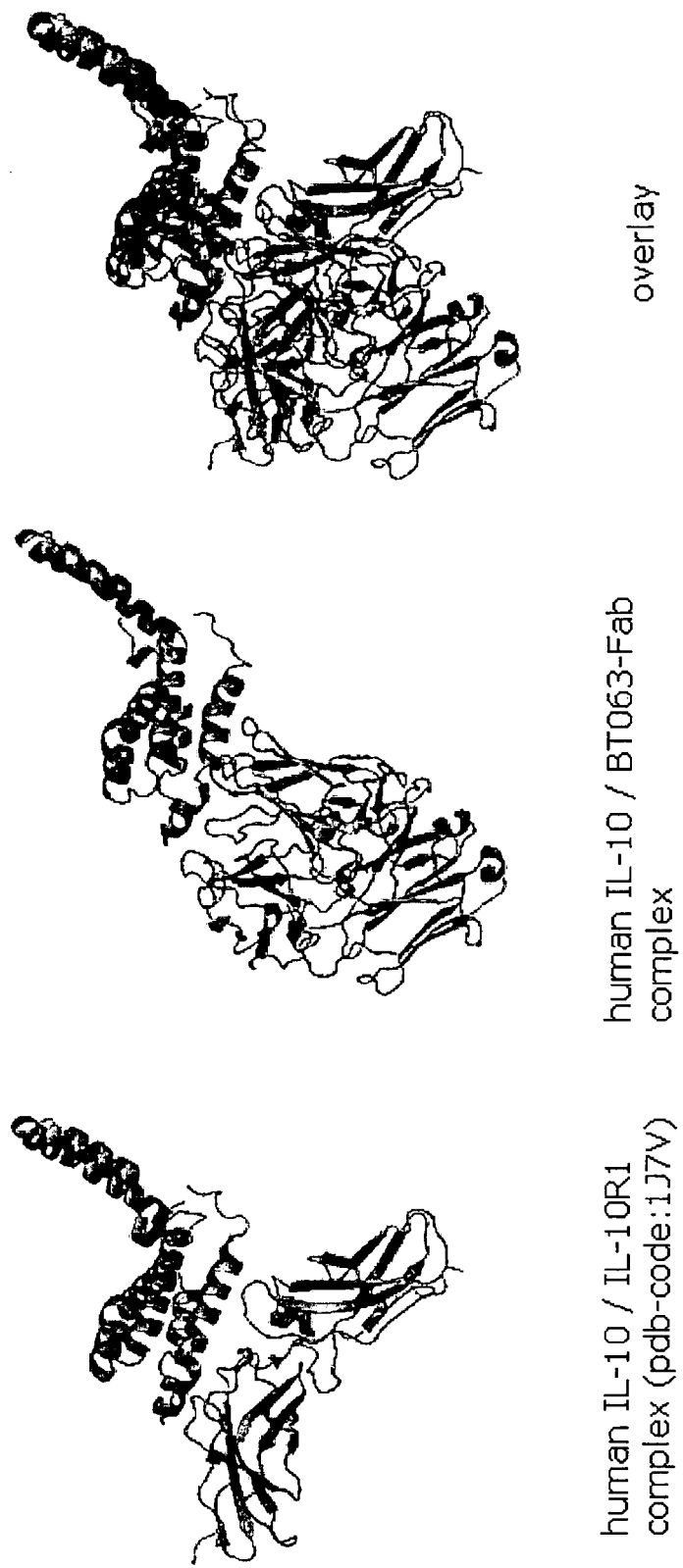

FIG. 9 shows the Fab fragment of BT-063 addresses the same binding site on IL-10 as the IL-10 receptor. IL-10, IL-10R1 and the Fab fragment are shown as a ribbon representation.

Figure 10:
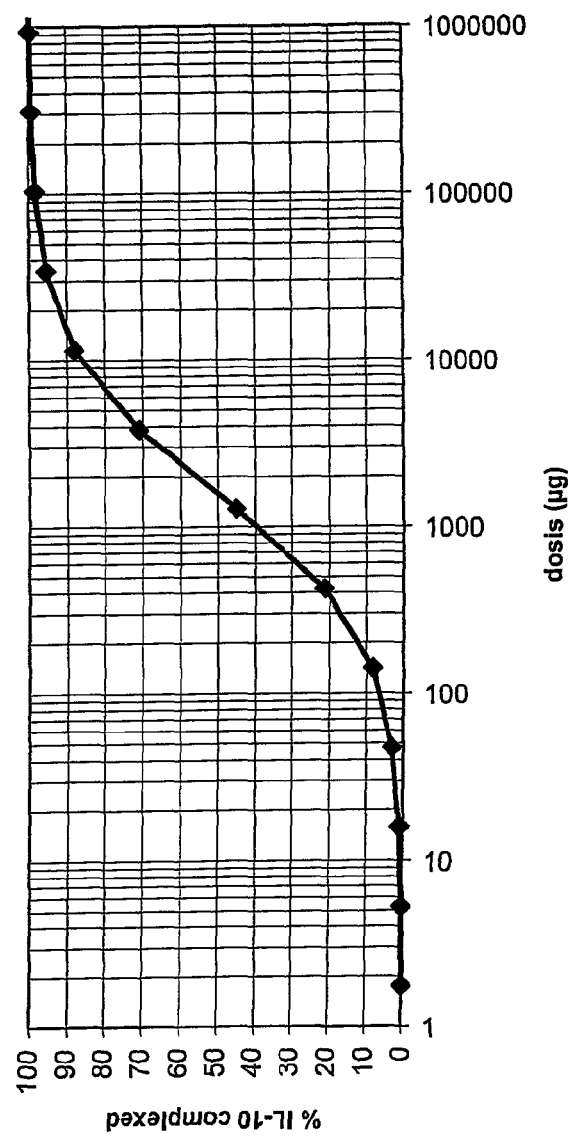

FIG. 10 shows the theoretically calculated dose dependency of IL-10 bound by increasing total doses of BT-063 after intravenous injection into healthy volunteers.

Figure 11:
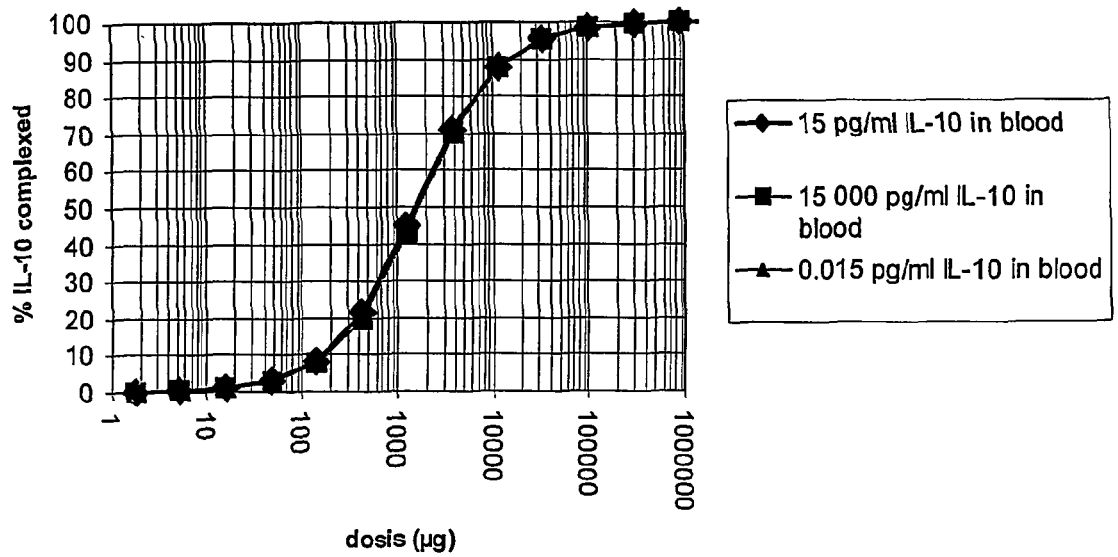

FIG. 11 shows the theoretical influence of different IL-10 concentrations on the dose-response curve depicted in FIG. 10. Curves for 1000 higher and lower concentrations as estimated as normal (15 pg/ml) are depicted. Only minor differences between the curves can be observed.

Figure 12:
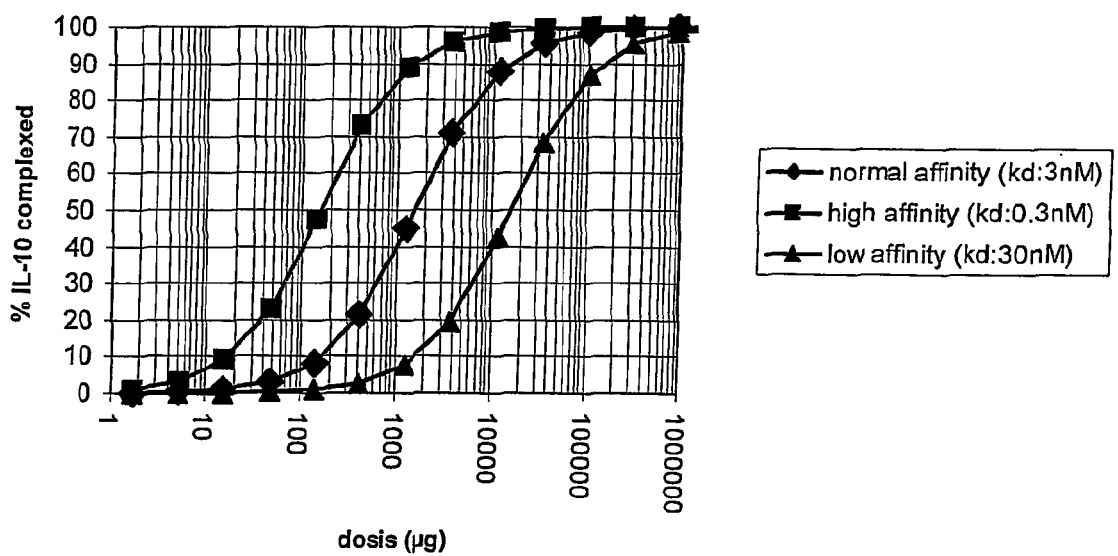

FIG. 12 shows the theoretical influence of different affinities of BT-063 to IL-10 on the dose-response curve depicted in FIG. 10. Curves for 10 fold higher and lower affinities as determined by BT-063 (3 nM) are depicted. The dose-response curve is largely dependent on the affinity of BT-063 to IL-10.

Figure 13:
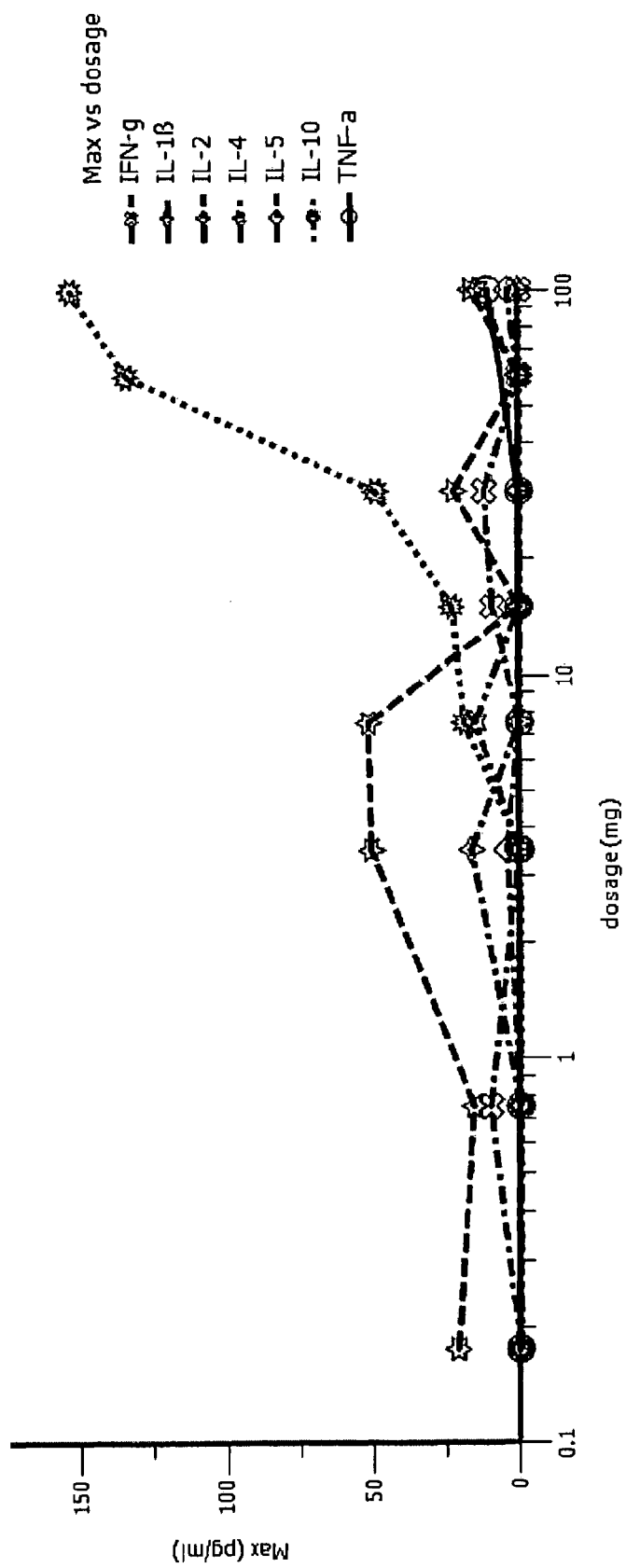

FIG. 13 shows a graph of mean cmax of cytokine concentration in plasma versus dosage after in vivo administration of BT-063 in healthy volunteers.

Figure 14:
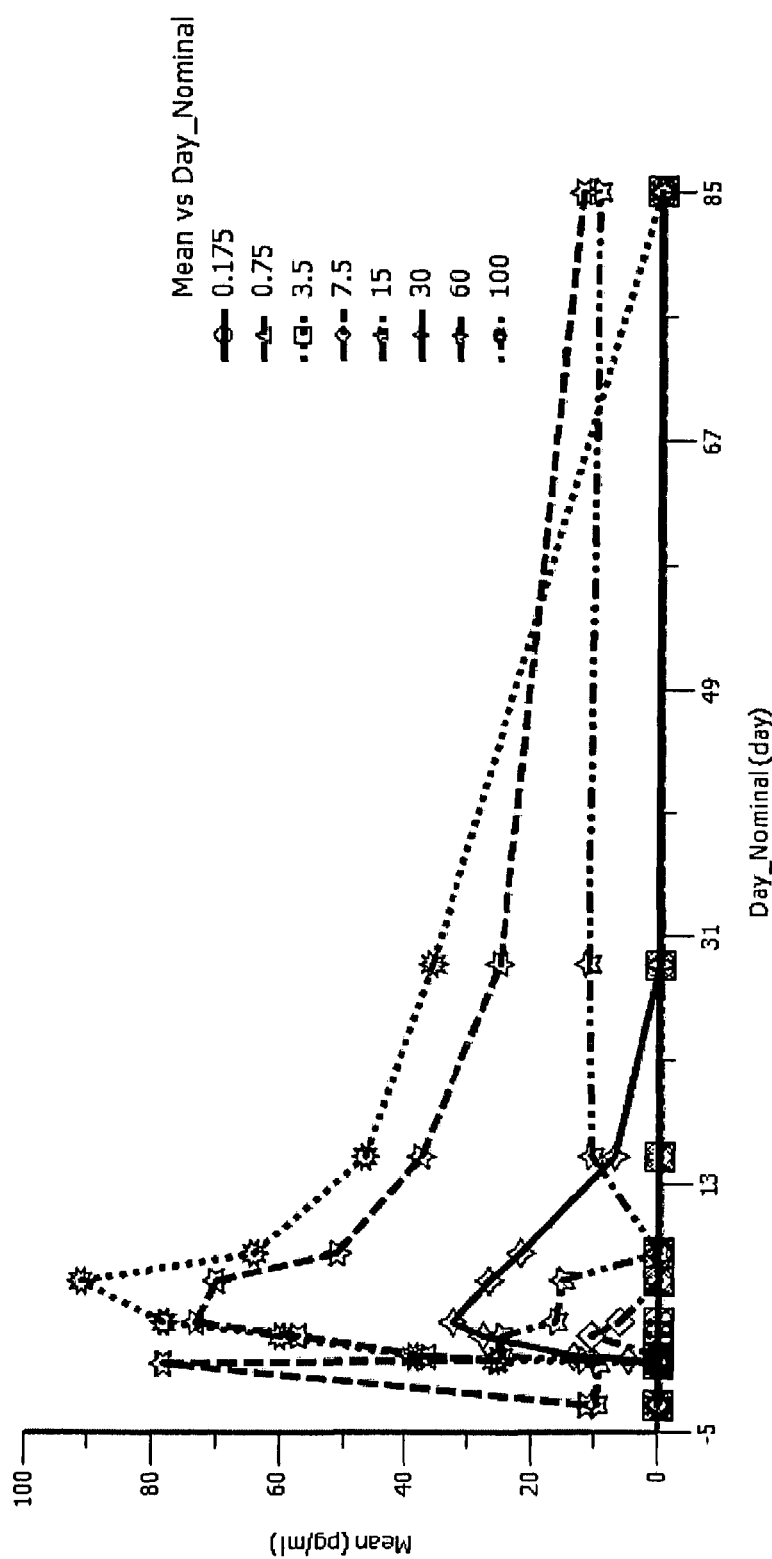

FIG. 14 shows a graph of mean IL-10 concentration in plasma over time after in vivo administration of BT-063 in healthy volunteers.

DETAILED DESCRIPTION OF THE INVENTION

As indicated above, the present invention relates to a humanized or chimeric antibody or fragment thereof capable of binding to interleukin-10 (IL-10), and the use of this antibody or fragment thereof in the treatment of medical conditions that are mediated by an elevated level or activity of IL-10.

Human IL-10 is a homodimer with a molecular mass of 37 kDa. Each monomer consists of 160 amino acids and has a molecular mass of 18.5 kDa. The IL-10 dimer interacts with the IL-10 receptor alpha (IL-Rα or IL-10R1) and subsequently recruits IL-10 receptor beta (IL-10Rβ or IL-10R2) into the complex. The receptor is expressed on a variety of cells, in particular immune cells (Asadullah et al., Pharmacol. Rev. 2003 June; 55(2):241-69) including most hematopoietic cells such as monocytes, macrophages, and T- and B-lymphocytes, but is also expressed on non-hemopoietic cells, such as epidermal cells or keratiocytes.keratinocytes. The binding of IL-10 receptor alpha by IL-10 and the recruitment of IL-10 receptor beta leads to signal transduction via Jak1 and Tyk2 tyrosine kinases and subsequently to activation of transcription factors of the STAT family. Various cellular sources of IL-10 are known, such as T helper cells, regulatory T cells, monocytes, macrophages, B cells, eosinophils, mast cells, keratinocytes, dendritic cells and even cancer cells. IL-10 functions on B cells range from prevention of apoptosis, enhancement of proliferation, class switching events and differentiation into plasma cells (Asadullah et al., Pharmacol. Rev. 2003 June; 55(2):241-69) and inhibition of inflammation.

In the first and second aspects of the present invention, and in preferred embodiments of the other aspects of the invention, the antibody or fragment thereof binds to the same region of IL-10 as the IL-10 receptor α (IL-10Rα) and is not capable of binding IL-10 when the IL-10 is bound to the IL-10 receptor, i.e. when IL-10 is bound to the antibody or fragment it is not able to bind to IL-10Rα.

As described above, the functionally active IL-10 dimer interacts with the IL-10Rα and subsequently recruits IL-10Rβ into the complex, which results in signal transduction. However, some suboptimal signalling events are expected to take place during the initial binding of the IL-10 to IL-10Rα.

Antibodies capable of neutralising the effects of IL-10 can operate via a number of mechanisms. They may bind to the IL-10 and prevent the binding of the IL-10 to IL-10Rα via steric hinderance.

In particular, since functionally active IL-10 is a homodimer, two antibody molecules may bind to the same IL-10 dimer. Alternatively it is possible that a neutralizing antibody binds to a region of IL-10 not overlapping with the IL-10Rα binding site and antagonizes the IL-10Rα binding by induced conformational changes in IL-10 (Josephson et al. Structure (2002) 10; 981-987) Alternatively, the antibodies may bind to a region of IL-10 which prevents interaction between the IL-10 and the IL-10Rβ. Further, it is also possible that an antibody binds to a site of IL-10 that is still exposed after binding of the cytokine to the high affinity receptor chain and induces a conformational change the hampers the recruitment of the second receptor chain necessary for signaling.

In contrast, the antibodies or fragments thereof of the present invention inhibit the interaction of the IL-10 with IL-10Rα by binding to the same region of the IL-10 as the IL-10Rα. Accordingly, the antibodies of the present invention prevent any binding between the IL-10 and the IL-10Rα. As such, even the suboptimal signaling events referred to above may be avoided. Accordingly, the present invention provides a humanized or chimeric antibody or fragment thereof capable of binding to interleukin-10 (IL-10), wherein said antibody or fragment thereof is capable of preventing IL-10 signaling through the IL-10α receptor.

The phrase "binds to the same region" as used herein refers to the ability of the antibody or fragment thereof to compete with the IL-10Rα for binding of IL-10. In effect the antibody or fragment thereof of the present invention acts as a competitive inhibitor. It is known that IL-10Rα binds to residues between 19 and 42 and between 138 and 158 in the IL-10 dimer. Accordingly, the antibody or fragment of the present invention is also capable of binding to at least one residue within both of these regions so as to effectively block IL-10Rα binding.

Further, the phrase "when IL-10 is bound to the IL-10 receptor" refers to the situation where IL-10 is bound with both sides, i.e. via both monomers, to the IL-10 receptor.

In a preferred embodiment the antibody or fragment thereof does not bind to the same region of IL-10 as the IL-10 receptor β (IL-10Rβ).

This aspect and embodiments of the present invention can alternatively be defined as the antibody or fragment thereof being capable of preventing IL-10 signalling through the IL-10α receptor, or as not being capable of binding to IL-1 OR expressing cells (i.e. via bound IL-10).

In the first and third aspects of the present invention, and in preferred embodiments of the other aspects of the invention, the antibody or fragment thereof binds to a discontinuous epitope comprising residues of one of the IL-10 homodimer's monomers and residues of the second IL-10 homodimer monomer, i.e. the antibody or fragment thereof binds to a discontinuous epitope comprising residues of the first monomer and residues of the second monomer, wherein the first monomer and the second monomer make up the homodimer.

The term "homodimeric form" refers to functionally active IL-10 represented by a symmetric homodimer composed of two alpha helical domains (domain A and domain B) oriented at 90 degrees to one another. The structural integrity of each domain is dependent on the intertwining of alpha helices from each peptide chain such that the first four helices of one chain associate with the last two helices of the other. A single IL-10 monomer is not able to bind to the IL-10 receptor, since parts of both chains are required in order to build the interface.

The antibodies and fragments thereof of the present invention exhibit concomitant interaction with both monomers of the wild type IL-10 dimer. As such, they bind to a "discontinuous epitope" i.e. an epitope in which amino acids are in close proximity in the folded protein, but distant when unfolded. In particular, the epitope is represented by amino acids present on both chains of the IL-10 dimer.

As a result of this mode of binding the antibodies and fragments thereof bind to the functionally active IL-10 with much greater affinity than to the IL-10 monomers, on which only a part of the discontinuous epitope is present.

In a preferred embodiment of the present invention the antibody or fragment thereof binds to a discontinuous epitope comprising residues of helix A of one IL-10 monomer (i.e. the first monomer) and residues of helix F' of the other IL-10 monomer (i.e. the second monomer).

In a particularly preferred embodiment of the present invention the humanized or chimeric antibody or fragment thereof binds to a discontinuous epitope provided by the first 55 amino acids of one IL-10 monomer, more preferably amino acids 20 to 55, and the last 20 amino acids of the second monomer and vice versa.

Artificial mutant forms of IL-10 combining helices A-D and helices E-F of one monomer in a from recognized by IL-10R1 or BT-063 are known from literature.

The IL-10 referred to herein is human IL-10, the amino acid sequence of which can be represented as:

```
                                              (SEQ ID NO: 1)
SPGQGTQSEN  SCTHFPGNLP  NMLRDLRDAF  SRVKTFFQMK

DQLDNLLLKE  SLLEDFKGYL  GCQALSEMIQ  FYLEEVMPQA

ENQDPDIKAH  VNSLGENLKT  LRLRLRRCHR  FLPCENKSKA

VEQVKNAFNK  LQEKGIYKAM  SEFDIFINYI  EAYMTMKIRN
```

It can be determined whether anti-IL10 antibodies have the desired activity by known peptide scanning techniques or by size exclusion chromatography.

Peptide screening techniques can consist of screening possible binders to IL-10, all or a fragment of which can be immobilized onto a membrane or on an adequate surface. In particular, the IL-10 or IL-10 fragment can be synthesized synthetically or the encoding nucleotide sequence can be overexpressed in an adequate host such as e.g. E. coli or insect cells. In particular, the regions of IL-10 identified herein as forming the epitope for the antibody of the present invention can be used.

Anti-IL 10 antibodies can be identified using e.g phage or ribosomal display (or mRNA display, polysomal display, yeast display) technology. With these technologies one can identify also binders recognizing discontinuous epitopes. Either the protein or the ligand (i.e. the antibody which will be selected) can be immobilized and incubated with the potential binding partner. Unbound proteins are removed and the bound ligands are eluted. Several rounds of selection will be carried out to identify high affinity binders.

Within the present application the term "chimeric antibody" refers to antibodies in which a portion of the heavy and/or light chain is identical with sequences in antibodies derived from a particular species or belonging to a particular antibody class or subclass, while the remainder of the antibody is identical with sequences in antibodies derived from a different species, antibody class or subclass. It is particularly preferred that the CDRs of a chimeric antibody have one origin, while the remainder of the antibody has a different origin. In particular, in the present invention the chimeric antibody may be a humanized antibody in which the antigen binding sequences/variable domains of a non-human antibody have been grafted onto human antibody framework regions.

Within the present application the term "fragment" refers to a fragment or a derivative of an antibody that still retains the desired biological activity. The fragment will generally comprise the antigen binding region of the antibody and, in particular, the Fab, Fab', F(ab)'$_2$, Fv and scFv fragments, as well as multivalent antibody derivatives, in particular diabodies or tandem diabodies. The fragment preferably is at least 25, more preferably 50 and still more preferably 200 to 500 amino acids. Alternatively, the fragments can be defined as those having of size of between 30 KDa and 150 kDa. Further, the antibody fragments may involve two or more peptide/polypeptide chains. For example an Fab fragment comprising two chains of between 200 and 300 amino acids in length each or TandAbs® (tetravalent bispecific antibody formats) comprising two chains of between 400 and 500 amino acids in length each.

In the fourth aspects of the present invention, and in preferred embodiments of the other aspects of the invention, the antibody or fragment thereof is derived from the murine B-N10 antibody or from BT-063 (variant hVH26/hVL7). In particular, such an antibody or fragment thereof will comprise CDRs being at least 80% identical to those of CDR 1, CDR 2 and CDR3 of the B-N10 or BT-063 variable light chain and/or comprises amino acid sequences at least 80% identical to those of CDR 1, CDR 2 and CDR3 of the B-N10 or BT-063 variable heavy chain. The amino acid sequence of the murine CDRs is shown in FIG. 1. The variable sequences of the BT-063 variant are show in Example 6. More preferably the sequences will be at least 90%, or at least 95% identical to those of the CDRs of the B-N10 or BT-063 antibody.

Alternatively, the antibody or fragment while still being derived from the B-N10 or the BT-063 antibody, can comprise an amino acid sequence of CDR 1, CDR 2 and CDR3 of the B-N10/BT-063 variable light chain and/or an amino acid sequence of CDR 1, CDR 2 and CDR3 of the B-N10/BT-063 variable heavy chain, optionally with variation in these sequences which does not substantially alter the affinity and/or specificity of the antibody or fragment thereof. In particular, the variations in the sequence do not reduce the affinity or specificity of the antibody or fragment for IL-10 as compared to that of an antibody or fragment comprising the CDRs of the murine B-N10 antibody or the BT-063 (variant hVH26/hVL7) antibody.

In a specific embodiment the humanized or chimeric antibody or fragment thereof comprises the amino acid sequences of CDR 1, CDR 2 and CDR3 of the murine antibody B-N10 variable light and/or heavy chains, or the BT-063 variant light and/or heavy chains. More preferably the present invention provides a humanized or chimeric antibody or fragment thereof which comprises amino acid sequences having at least 80%, more preferably at least 90% most preferably at least 100% sequence identity with the variable domains of the murine antibody B-N10, as shown in FIG. 1, or with the variable domains of the BT-063 antibody as shown in Example 6.

Still further, as a result of the X ray crystallography studies performed by the present inventors the antibody or fragment thereof of the present invention can also be defined as a humanized or chimeric antibody or fragment thereof capable of binding to IL-10, wherein said antibody or fragment thereof comprises a variable region comprising CDR1 and CDR2 of BT-063 light chain and/or a variable region comprising CDR1, CDR2 and CDR3 of BT-063 heavy chain optionally with amino acid substitutions in the sequences of the CDRs provided:

(i) the light chain CDR1 comprises: Ser32, Asn33, Asn35, Tyr37
(ii) the light chain CDR2 comprises: Lys55
(iii) the heavy chain CDR1 comprises: Phe27, Ser28, Ala30, Thr31, Tyr32
(iv) the heavy chain CDR2 comprises: Trp52, Arg53, Gly54, Ser56
(v) the heavy chain CDR3 comprises: Tyr100, Gly101, Tyr103.

More preferably the heavy chain variable region further comprises Asn73 and Ser74. It is particularly preferred that with the substitutions within the CDRs their sequence is at least 80%, more preferably at least 90% identical, to that of the CDRs in BT-063.

The use of residue type and number has been done for the purpose of clearly identifying the amino acid residue of the BT-063 CDR which is being referred to. However, it will be appreciated that the number of the residue is not intended to limit the residue to being in that position in the candidate antibody or fragment being screened in the method. For example, in an antibody of this embodiment Ser32 may be at position 31 within a light chain CDR1 if a non-essential amino acid residue has been deleted from the section 1 to 30 of the light chain.

The sequences of BT-063 heavy and light chains and the positions of the CDRs are shown in Example 6 below.

In a fifth aspect of the present invention, and in preferred embodiments of the remaining aspects of the invention, the humanized or chimeric antibody or fragment thereof capable of binding to interleukin-10 (IL-10) does not induce antibody-dependent cell-mediated cytotoxicity (ADCC) and/or complement-dependent cytotoxicity (CDC).

As indicated above, the antibody or fragment is not capable of binding to IL-10 when IL-10 is bound to the IL-10 receptor α. Accordingly, the antibody or fragment thereof can only bind to soluble IL-10 and are not able to bind to IL-10R expressing cells (via IL-10). As a result, the antibody or fragment of the present invention is not able to induce ADCC or CDC, at least partly due to its property to only bind to soluble IL-10 and not cell bound IL-10.

For testing whether an antibody induces CDC, cells carrying the antigen of interest can be incubated with increasing doses of the antibody in the presence of complement (or serum which contains active complement such as C1q). The degree of cell killing can be measured as parameter describing the amount of CDC induced.

For testing whether an antibody induces ADCC, cells carrying the antigen of interest (target cells) can be incubated with increasing doses of the antibody in the presence of ADCC inducing cells (e.g. natural killer cells, effector cells). The degree of cell killing on the target cells can be measured as parameter describing the amount of ADCC induced.

In addition, in a further aspect of the present invention and in preferred embodiments of the remaining aspects of the invention, the humanized or chimeric antibody or fragment thereof is capable of binding to interleukin-10 (IL-10) such that when it is administered to a patient at least 50%, more preferably at least 60%, most preferably at least 75% of the IL-10 in the patient's plasma is complexed with the antibody or fragment thereof. In this context, the term "complexed with the antibody or fragment thereof" refers to the IL-10 occupancy by the antibody or fragment thereof after it has been administered to the patient. The IL-10 occupancy capacity of an antibody or fragment can be assessed in vitro based on a blood volume of 3.51, and with knowledge of the dissocation constant between the antibody or fragment and IL-10, and further, using the assumptions and methods provided in Example 8, below.

Generally, the antibody of the invention further comprises a human constant region (Fc). This can be selected among constant domains from any class of immunoglobulines, including IgM, IgG, IgD, IgA and IgE, and any isotype, including IgG1, IgG2, IgG3 and IgG4. Preferred constant regions are selected among the constant domains of IgG, in particular IgG1.

Other Products

The present invention further provides nucleic acid sequences encoding the antibody or antibody fragments described above. The nucleic acid sequences may be DNA or RNA but are preferably DNA. The sequences may be used within expression cassettes or vectors, and are of particular use in producing the antibodies and fragments thereof disclosed herein.

The invention further provides host cells transformed with these polynucleotides, expression cassettes or vectors. Suitable host cells can be both prokaryotic and eukaryotic.

Alternatively, the host cell can be a hybridoma obtained by fusing a cell producing an antibody of the present invention with a myeloma cell.

The host cells described above can be utilized in a method for the production of an antibody or fragment thereof. In particular, such a method may comprise a step of culturing the host cell in a suitable culture medium under conditions allowing the expression of the antibody or fragment thereof and separating the antibody or fragment from the culture medium. Methods of this type are well known and described in the art.

The present invention also provides an isolated peptide comprising less than 50 amino acids comprising one or both of amino acids 27 to 53 and amino acids 142 to 155 of human IL-10. Such peptides are of particular use in the screening methods described below.

Medical Uses

The antibodies and fragments thereof described herein have utility in the treatment of diseases or medical conditions which are mediated by an elevated level or activity of IL-10. As a result, provided is a method for treating or preventing a medical condition in a subject, wherein the medical condition is mediated by an elevated level or activity of IL-10, comprising administering a therapeutically effective amount of the antibody or fragment thereof described herein.

In particular, the medical condition which is mediated by an elevated level or activity of IL-10 is SLE. Accordingly, the present invention also provides an antibody or fragment thereof as described herein for use in medicine, and in particular in the treatment of SLE.

Further examples are thrombocytopenic purpura, lupus nephritis, HIV, hCMV, and hepatitis C. The treatment of tumor cells depending on IL-10 by direct support of proliferation or suppression of immune response is another example.

A further embodiment of the invention is a pharmaceutical composition comprising the antibody or fragment thereof described above with a pharmaceutically acceptable carrier or diluent. In an embodiment, the composition comprising liposomes to which the antibody or fragment thereof is coupled.

Such compositions can be administered to the patient parenterally, intravenously or subcutaneously. Preferably in the treatment of SLE the antibody or fragment thereof is administered intravenously or subcutaneously.

In addition, the antibodies and fragments thereof described herein have utility in diagnosis of medical conditions which are mediated by an elevated level or activity of IL-10. In particular, the antibodies and fragments thereof can be utilized in in vitro assays to determine the presence of an abnormal level of IL-10 in samples taken from individuals. Such methods of diagnosis can comprise: (a) obtaining or providing a sample taken from an individual; (b) contacting the sample with an anti-IL-10 antibody or fragment thereof as described herein; and (c) detecting the presence of IL-10 (for example by detecting the presence of the antibody or fragment thereof). In particular, step (c) can involve determining the amount of IL-10 present in the sample. In addition, the method may further comprise a step (d) of comparing the amount of IL-10 present to one or more pre-determined values in order to make an assessment regarding the patient and the medical condition. The pre-determined values may represent a standard value of the amount of IL-10 present in an equivalent sample taken from a healthy individual.

Preferably the sample is a plasma sample obtained by taking blood from the individual. In particular, the method of diagnosis can be used where the medical condition is SLE.

Non-Medical Uses

Still further provided is a labeled humanized or chimeric antibody or fragment thereof comprising the antibody or fragment thereof described herein and a label. The label may be of any suitable type known in the art for detecting the presence of an antibody in a sample. In particular, the label may be a fluorescent label.

The antibody or fragment thereof of the present invention, and in particular the labeled antibody, has specific utility in an in vitro method for detecting the presence of IL-10 in a sample. The method may comprise a step of contacting the unlabelled or labeled antibody or fragment thereof with the sample, washing the sample to remove antibody or antibody fragments which are not bound to the sample (unbound antibody or antibody fragments) and detecting the presence of the antibody, for example via the label, in the sample.

Alternatively, the unlabeled antibody or fragment may be used for an in vitro method for neutralizing IL-10 in a sample. Such a method comprises the steps of contacting the sample with the antibody or fragment thereof so as to bind the antibody or fragment thereof to the IL-10.

Further, the present invention also provides a method for screening for one or more molecules capable of binding to the same region of IL-10 as the IL-10 receptor α (IL-10Rα) comprising:

(a) contacting the one or more molecules with a peptide comprising one or more of the following regions of human IL10: amino acids 27 to 53 and amino acids 142 to 155; and (b) detecting whether the one or more molecules binds to the one or more regions of the peptide.

In particular the one or more molecules are preferably peptides, and are most preferably antibodies or antibody fragments. Screening can be completed by methods which are known in this art, such as through the generation and screening of a phage display library.

Still further, the present invention provides a method for screening for an antibody or antibody fragment capable of binding to the same region of IL-10 as the IL-10 receptor α (IL-10Rα) comprising:

(a) contacting one or more antibody or antibody fragments with IL-10;

(b) assessing the ability of the antibody or antibody fragment to inhibit the interaction between IL-10 as the IL-10 receptor α (IL-10Rα);

(c) identifying an antibody or antibody fragment which is capable of binding to the same region of IL-10 as the IL-10 receptor α (IL-10Rα), wherein the antibody or antibody fragment comprises a variable region comprising CDR1 and CDR2 of BT-063 light chain and/or a variable region comprising CDR1, CDR2 and CDR3 of BT-063 heavy chain, optionally with amino acid substitutions in the sequences of the CDRs provided: (i) the light chain CDR1 comprises: Ser32, Asn33, Asn35, Tyr37

(ii) the light chain CDR2 comprises: Lys55

(iii) the heavy chain CDR1 comprises: Phe27, Ser28, Ala30, Thr31, Tyr32

(iv) the heavy chain CDR2 comprises: Trp52, Arg53, Gly54, Ser56

(v) the heavy chain CDR3 comprises: Tyr100, Gly101, Tyr103.

In this aspect the work of the present inventors has provided details on which molecules are likely to have the ability to bind to IL-10 and accordingly a method of screening with particular candidate molecules is possible. The candidate molecules can be generated through the targeted mutagenesis of the nucleotide sequence encoding the variable regions of the BT-063 antibody.

The invention will now be described further in relation to the following specific embodiments.

EXAMPLES

Example 1

Characterisation of Murine Anti-IL10 Antibody B-N10

1.1. Isolation of DNA Encoding the Variable Antibody Domains of B-N10

For the identification of the variable sequences of murine BN-10 cell pellets were used. The samples (3×B-N10, Passage 3, 1×10$^7$ cells) were stored at −80° C. until mRNA was isolated from the cells and, after cDNA synthesis, the variable sequences of B-N10 were amplified by PCR and then cloned.

In total 14 clones were sequenced (SEQ Laboratories, Göttingen) and analysed for both the variable light chain and for the variable heavy chain. The variable sequences of the B-N10 were determined unequivocally. Deviations occurred only in the N-terminal primer regions (see Table 1). In the case of the variable heavy chain, the sequence variant QVQLKQ (SEQ ID No: 59) occurred nine times in the primer region, but other variations occurred only once or twice. This variant was chosen for subcloning. In the case of the variable light chain, two variants were present in equal proportions. After comparing the sequences with the murine germ line sequences, the crl sequence with only 3 mutations exhibited great homology with the identified VL sequence. This means that the DVLMTQ (SEQ ID No: 60) sequence is most probably the correct sequence. The sequence DIVMTQ (SEQ ID No: 61) is typical of another class of germ line sequence and was therefore excluded.

TABLE 1

Occurrence of N-terminal sequence variants of the sequenced variable light and heavy chain of B-N10.

| | Sequence | Number |
|---|---|---|
| Variable light chain | DIVMTQ (SEQ ID No: 61) | 5 |
| | DVLMTQ (SEQ ID No: 60) | 5 |
| | DVLMTR (SEQ ID No: 62) | 1 |
| | DIVITQ (SEQ ID No: 63) | 1 |
| | DIVLTQ (SEQ ID No: 64) | 2 |
| Variable heavy chain | QVQLKQ (SEQ ID No: 59) | 9 |
| | QVQLKE (SEQ ID No: 65) | 2 |
| | EVQLQQ (SEQ ID No: 66) | 1 |
| | QVQLNQ (SEQ ID No: 67) | 1 |
| | QVQLTQ (SEQ ID No: 68) | 1 |

The chosen sequences are indicated in bold type.

The protein sequences of the variable light chain VL and variable heavy chain VH are shown in FIGS. 1A and 1B, respectively. The hypervariable complementarity-determining regions (CDRs) are underlined. The corresponding DNA sequences are shown in FIGS. 2A and 2B, respectively.

Example 2

Generation of a Chimeric B-N10 Antibody

The identified variable sequences of the heavy and light antibody chain from Example 1 were cloned into a vector system for the expression of recombinant antibodies. The first step was to clone the sequences into a BS leader; the N terminal adds a secretion signal and the C terminal adds a splice-donor sequence. The second step was to clone these sequences into the expression vectors which contain the constant human kappa chain and the constant human gamma-1 chain respectively. The vector for the light chain and the vector for the heavy chain were prepared and then transiently co-transfected into COS-7 cells by calcium phosphate precipitation or by lipofection. The cell culture supernatant was harvested after 2 days. After expression of the chimeric B-N10 in COS-7 cells and detection of an antibody titre in the supernatant (sandwich ELISA), its specific binding capacity to human interleukin 10 (R&D Systems, Cat. No. 217-IL/CF, Lot ET 114021, stored at −20° C.) was tested in the ELISA.

For the sandwich ELISA a mouse anti-human kappa chain antibody (Becton Dickinson) was bound to the plate surface as a catcher antibody, then incubated with cell culture supernatant and the presence of the chimeric antibody was detected with a POD-conjugated rabbit anti-human IgG (H+L) antibody (Dianova). A chimeric control antibody in defined concentrations (0.125 to 12 g/mL) was used as a positive control.

For the antigen ELISA, human IL-10 was bound to the plate surface in a concentration of 0.5 and 5 µg per mL. After incubation with the cell culture supernatant (undiluted and diluted 1:5), the binding of the chimeric B-N10 was detected with the POD-conjugated rabbit anti-human IgG (H+L) antibody (Dianova). The murine B-N10 was used as a positive control. The antibody was used in a concentration of 0.5 and 5 µg per mL and binding was detected with a POD-conjugated rabbit anti-mouse IgG/IgM antibody (Dako).

The results of the ELISA are discussed in Example 3.

Example 3

Humanization of Anti-IL10 Antibodies

Initial efforts to reduce the immunogenicity of rodent antibodies in humans involved the generation of chimeric antibodies by replacing rodent by human constant antibody domains. As the rodent framework regions within the variable domains might still induce an immune response the more advanced method of CDR grafting was developed, meaning the transfer of the antigen binding sequences (complementarity determining regions, CDR) onto completely human antibody frameworks (humanization). Usually human acceptor frameworks are selected that resemble most closely the murine donor antibody to increase the probability of restoring the original antigen specificity and affinity during the humanization process. Different approaches using human antibody germline sequences, consensus sequences of expressed antibodies, analysis of CDR loop structures and X-ray structures of antibody/antigen complexes might be used or combined to improve the process. Usually several humanized antibody variants are generated in this way and analysed afterwards regarding their biological effects which might differ from each other and the original antibody. Finally according to the desired function of the antibody a suitable human constant region might be selected.

3.1 Sequence Comparisons Between the Murine Variable Sequences of B-N10 and Human Sequences, and Design of a Set of Humanized VL (hVL) and VH (hVH) Sequences The murine anti-IL10 antibody B-N10 was selected (Llorente et al., Eur. Cytokine Netw. 1993 November-December; 4(6):421-7; and Llorente et al., Arthritis Rheum. 2000 August; 43(8):1790-80). The method for obtaining humanized antibodies is based on the CDR-grafting procedure where the complementary determining regions (CDRs) are fused to human acceptor regions.

The choice of human acceptor frameworks was based on a combined analysis of three data sets:
1. The homology of the murine sequences to human germline sequences to minimize risk of somatic mutations:
2. The comparison of the murine sequences to human consensus sequences to identify unusual amino acid residues and
3. The identification of the canonical structure classes of the CDR sequences to obtain information about important structural framework amino acid residues.

The murine variable light chain of the B-N10 shows the highest homology to the human germline variable segment 2-30*01 (A17 (SEQ ID No: 14)) and to the joining segment JK1 (SEQ ID No: 15). The human consensus sequence with highest homology to B-N10 is HuKII. Complementarity determining regions (CDRs) of the variable light chain could be classified in case of L1 to class 4, and in cases of L2 and L3 to class 1. Critical amino acid residues were identified.

Sequence comparison between mouse CDR and human germline VL genes with the canonical structure of class 4-1-1 revealed highest homology with 2-30*01 (the lowest number of mismatching amino acids).

The murine variable heavy chain of the B-N10 shows the highest homology to the human germline variable segment VH3-33 and to the joining segment JH4 (SEQ ID No: 17). The human consensus sequence with highest homology to B-N10 is HuHIII. Complementarity determining regions (CDRs) of the variable heavy chain could be classified in case of H1 and H2 to class 1. Critical amino acid residues were identified. Sequence comparison between mouse CDR and human germline VH genes with the canonical structure of class 1-1 revealed highest homology with 3-66*04 (SEQ ID No: 16) (the lowest number of mismatching amino acids). Therefore, the germline sequence VH3-66 was taken too in consideration.

All data obtained were considered to design a set of different variable sequences of humanized variable light (12 variants) and variable heavy chains (29 variants).

3.2 Construction of a Small Library and Selection of Humanized hIL-10 Binding Antibody Fragments In order to generate a library of potentially hIL-10 binding antibody fragments to achieve the optimal human IL-10 binding antibody, the cDNA sequences coding for the 12 hVL and the 29 hVH fragments, as shown in FIG. 3, were generated under consideration of the codon usage of eucaryotic cells.

The obtained cDNAs were cloned subsequently into cloning vectors and sequenced at SEQ Laboratories (Göttingen, Germany). The library was constructed in a way, that each of the 12 cDNAs coding for the hVL fragments were combined with the 29 cDNAs coding for the hVH fragments resulting in 348 potentially expressed antibody fragments.

Following the bacterial expression and two rounds of selection on human IL-10 (R&D Systems, Cat.-No. 217-IL/CF) the antibody fragments were analysed by ELISA for binding to hIL-10 (same as for selection). In brief, Maxisorb plates (Nunc, Germany) were coated with 1 µg/ml hIL-10 in PBS over night at 4° C. After blocking and washing of the plates, the supernatants of the antibody fragment producing bacteria were added. For detection of bound humanized antibody fragments a POD conjugated secondary antibody was used.

The coding sequences of good binders were analyzed and the occurrence of identified hVL- and hVH-fragments listed (Table 2).

TABLE 2

Occurrence of VL and VH fragments present in antibody fragments binding to hIL-10.

| Occurrence of variable heavy chain variants hVH variant | Occurrence | Occurrence of variable light chain variants hVL variant | Occurrence |
|---|---|---|---|
| hVH1 | 1 | hVL1 | 2 |
| hVH5 | 1 | hVL2 | 1 |
| hVH7 | 2 | hVL3 | 1 |
| hVH9 | 2 | hVL5 | 1 |
| hVH12 | 1 | hVL6 | 3 |
| hVH13 | 2 | hVL7 | 4 |
| hVH14 | 1 | hVL8 | 18 |
| (hVH16) | 4 | (hVL9) | 4 |
| hVH18 | 4 | hVL10 | 1 |
| hVH20 | 4 | hVL11 | 1 |
| hVH21 | 1 | hVL12 | 2 |
| hVH23 | 1 | | |
| hVH26 | 9 | | |
| hVH27 | 2 | | |
| hVH28 | 3 | | |
| hVH29 | 1 | | |

Sequences marked in bold were selected for subcloning into the appropriate eukaryotic expression vectors to analyze the binding properties in the context of the entire antibody. The sequences shown in brackets were selected for subcloning into the expression vectors but the procedure only resulted in defective constructs.

3.3 Generation of Expression Vectors for the Selected Humanized Light and Heavy Chain Variants of BT-063

Based on the statistics determined by the screening approach a set of humanized VL and humanized VH variants of BT-063 were selected for cloning into a vector system. In a first step, the cDNAs encoding the humanized VL and VH variants were transferred into an appropriate vector in order to fuse a sequence coding for a secretory signal 5' and a splice donor sequence 3' to the cloned cDNA. These cDNA constructs were, in a second and final subcloning step, transferred into the expression vectors encoding the human constant kappa and the human constant gamma-1 chain, respectively. Plasmids of independently obtained hVL and hVH containing expression vectors were prepared by the endotoxin-free Qiagen Midi-prep kit (Qiagen, Germany).

3.4 Transient Expression of the Selected Humanized BT-063 Variants in COS-7 Cells and Comparison of Antibody Binding Towards hIL-10

For the transient expression of the humanized antibody variants in COS-7 cells each of the selected humanized VL variants (hVL7 and hVL8) was combined with each of the selected humanized VH variants (hVH1, hVH9, hVH13, hVH18, hVH20, hVH26, hVH28) resulting in 14 different humanized antibodies.

In brief, the expression vectors coding for the light chain and for the heavy chain were transiently cotransfected into COS-7 cells by calcium phosphate precipitation in DMEM containing 10% FCS in a 24-well format. After transfection the medium was replaced by the serum free medium CHO—S-SFM II (Invitrogen, Germany) and the supernatants of the COS-7 cells were collected 2-3 days after transfection. The antibody titer of the humanized antibodies secreted into the supernatants of transfected COS-7 cells were analyzed by a sandwich ELISA. Based on the determined antibody concentrations supernatants of all samples were adjusted to the same antibody concentrations, and all samples were used to analyze binding to human IL-10 in an antigen ELISA, whereby Maxisorb plates (Nunc, Germany) were coated with 2 µg/ml hIL-10 in PBS.

As shown in FIG. 4, all analyzed variants bind to hIL-10, however with different binding properties. Significantly the highest signals in the antigen ELISA were obtained with the BT-063 variants hVH20/hVL7, hVH26/hVL7 and hVH20/hVL8 showing signal intensities comparable to that obtained with the chimeric B-N10 antibody. Within these three antibodies variations in signal intensities (higher signal for hVH20/hVL8 and lower signals for hVH20/hVL7 and hVH26/hVL7) could be caused by divergent antibody concentrations as a result of the quantifying sandwich ELISA (see above). All other investigated variants resulted in rather weak signals compared to the chimeric B-N10 antibody.

3.5 Production and Affinity Purification of the Chimeric and Humanized Antibody Variants The selected humanized BT-063 variants (hVH20/hVL7, hVH20/hVL8, hVH26/hVL7) and the chimeric cB-N10 (discussed in Example 2) were produced in COS-7 cells.

Transient expression was performed as described in section 3.4 whereby 10 cm tissue plates were used. Serum-free supernatants of approximately 0.5 L of each variant were collected 5 days post transfection.

Purification of the antibodies was performed by protein A affinity chromatography from serum free supernatants. Supernatants were loaded in the presence of 2M NaCl. Antibodies were eluted by a 0.1M Citrat buffer pH 4.0 and fractionated into tubes containing 2M phosphate buffer pH 7.2. Buffer exchange against PBS as well as concentration of individual antibody probes was performed by centrifugation using membranes of a 30 kDa cut off. The quality of purified materials was checked by antigen ELISA, SDS-PAGE under non-reducing as well as reducing conditions and UV measurement at 260 nm and 280 nm.

Binding towards hIL-10 of the purified chimeric B-N10 and the humanized variants was tested by ELISA according to the method as described above in Example 2. hIL10 was coated and the antibody binding was measured for the variants cB-N10, BT-063-1 (hVH20/hVL7), BT-063-2 (hVH20/hVL8) and BT-063-3 (hVH26/hVL7). The results are shown in FIG. 5.

The signal intensities were comparable for the chimeric B-N10 and the hVH20/hVL7 variant, whereas the signal intensities of the variants hVH20/hVL8 and hVH26/hVL7 were slightly less.

3.6 Affinity Determination by Biacore Human IL-10

Surface plasmon resonance analysis was used to measure the association and dissociation rate constants for binding of the different antibodies (murine, chimeric, 3 humanized variants) towards hIL-10 using BIACORE 2000 (Biacore AB, Uppsala, Sweden). hIL-10 was immobilized on a CM-5 sensor chip according to manufacturers conditions. hIL-10 was immobilized by adding a 50 µl aliquot of 20 µg/ml at a flow rate of 5 µl/minute resulting in an immobilization density of 320 RU. The immobilized hIL-10 surface was regenerated in a two step cycle by using 0.1M carbonate buffer pH 9.2 and 0.01M HCL/1M NaCl at flow rates of 50 µl/minute for one minute each. Each antibody sample was analyzed at least 4 times in antibody concentration ranges of 20-0.15 µg/ml. Calculations from the sensograms were performed by using the BIA evaluation version 3 (1999) software.

Table 3 summarizes the results of all Biacore measurements. All variants bind comparable to hIL-10. However, slight differences are detectable. As a result the mouse monoclonal antibody B-N10, the chimeric cB-N10 as well as the humanized variant BT-063-1 (hVH20/hVL7) bind with comparable affinities whereas the two other humanized variants BT-063-2 (hVH20/hVL8) and BT-063-3 (hVH26/ hVL7) show reduced affinities (about factor 3 compared to the murine B-N10). Slight differences in association and dissociation rates are also detectable.

TABLE 3

Results of Biacore measurements

| Antibody variant | n | ka [1/Ms] | kd [1/s] | KD [M] ± SD |
|---|---|---|---|---|
| B-N10 | 6 | 4.43 E6 | 2.05 E−3 | 1.07 E−9 ± 3.11 E−10 |
| cB-N10 | 4 | 6.23 E5 | 8.48 E−4 | 1.37 E−9 ± 2.42 E−10 |
| BT-063-1 | 6 | 1.21 E6 | 1.03 E−3 | 1.22 E−9 ± 1.44 E−10 |
| BT-063-2 | 4 | 1.21 E6 | 1.64 E−3 | 2.81 E−9 ± 1.03 E−9 |
| BT-063-3 | 5 | 1.07 E6 | 2.66 E−3 | 2.91 E−9 ± 8.07 E−10 | n = number of individual measurements; ka = association rate; kd = dissociation rate; KD = dissociation constant Cynomolgus IL-10

The affinity of the BT-63 variant 3 (hVH26/hVL7) to Cynomolgus IL-10 was analysed by additional surface plasmon resonance experiments using a Biacore T100 (Biacore AB, Uppsala, Sweden).

BT-063 was diluted in 10 mM acetate pH5.5 to 5 μg/mL and immobilized using amine coupling procedure to obtain a final level of about 1000 RU. Regeneration of the sensor chip surface was obtained injecting 10 mM Glycine-HCl pH 1.8 for 30 s. Samples were injected in different concentrations over the flow cell as well as over the reference cell. Signals obtained by the reference cell were subtracted from the signals obtained by the detector flow cell and resulting binding profiles were evaluated using a 1:1 Langmuir-binding model. A concentration depending binding profile was obtained and an average KD of 194 pM was calculated for Cynomolgus IL-10. As a positive control rhIL-10 was analysed resulting in a KD of 4.6 nM. Results are summarized in Table 4.

TABLE 4

Results of Biacore measurements with BT-063 rhIL-10: recombinant human IL-10; rCIL-10: recombinant Cynomolgus IL-10;

| Analyte | Assay no | ka [1/Ms] | kd [1/s] | KD [M] |
|---|---|---|---|---|
| rhIL-10 | 1 | 6.0 E5 | 0.3 E−2 | 4.6 E−9 |
| rCIL-10 | 1 | 6.2 E7 | 1.2 E−2 | 0.196 E−9 |
| rCIL-10 | 2 | 8.6 E7 | 1.7 E−2 | 0.195 E−9 |
| rCIL-10 | 3 | 9.7 E7 | 1.8 E−2 | 0.191 E−9 | ka = association rate; kd = dissociation rate; KD = dissociation constant

Example 4

Activity of Anti-IL10 Antibodies In Vitro

To confirm the potency of BT-063 (variant hVH26/hVL7) the blockade of IL-6 release in peripheral blood mononuclear cells (PBMCs) was examined. PBMCs release Interleukin-6 (IL-6) upon stimulation with Lipopolysaccharide (LPS). A physiological activity of Interleukin-10 (IL-10) is the inhibition of secretion of cytokines, e.g. IL-6. Thus, IL-10 addition to LPS stimulated cells inhibits IL-6 secretion, leading to a significant reduction of IL-6 present in the medium of the cell culture. However, as a consequence of BT-063 addition to the cell culture, IL-10 is bound and thus not able to bind to the receptor on the cell surface. The inhibitory effect of IL-10 is compensated and IL-6 secretion is restored, leading to IL-6 in the medium.

PBMCs were isolated from human blood by Ficoll gradient. The isolated cells were seeded at 1×10$^6$ cells/ml and stimulated with LPS for IL-6 secretion, which was inhibited by addition of IL-10. The inhibitory effect of IL-10 was neutralized by addition of BT-063, thus reconstituting IL-6 secretion. Depending on the purpose (reference or low, high quality control samples) of added BT-063, different titration concentrations of BT-063 were used, leading to concentration dependant secretion of IL-6 which were detected in the supernatant of the cell culture.

TABLE 5 mean values of IL-6 levels from double determinations and IL-6 reconstitution respectively in dependence of titration of reference standard

| S1: 40 μg/mL concentration of BT-063 [μg/mL] | mean value of IL-.6 level [μg/mL] | Reconstitution of IL-6 Secretion [%] |
|---|---|---|
| 40.000 | 42546 | 72.8% |
| 20.000 | 43134 | 73.8% |
| 13.333 | 37910 | 64.9% |
| 8.889 | 31107 | 53.2% |
| 5.926 | 25602 | 43.8% |
| 3.951 | 20793 | 35.6% |
| 1.975 | 14200 | 24.3% |
| 0.988 | 10227 | 17.5% |

As shown in Table 5, the amount of secreted IL-6 is directly correlated with the concentration of BT-063. The higher the concentration of BT-063, the more IL-6 was secreted from the PBMCs and thus present in the supernatant. Incubation of the cells with 40 μg/mL BT-063 led to a reconstitution of IL-6 secretion of about 73%, whereas with 0.988 μg/mL BT-063 (last step of titration) only 17.5% of the IL-6 level was detectable in the medium when compared to the positive control (stimulated PBMCs without IL-10 incubation).

Example 5

Binding of Antibody to Human PBMC

Human peripheral blood mononuclear cells (PBMC) were freshly prepared from different healthy volunteers using gradient centrifugation. For this purpose blood samples were diluted 1:1 with Hanks buffered solution and 20 ml Ficoll was slowly overlaid with 20 ml of this solution in a sterile 50 ml tube. The tubes were centrifuged at room temperature for 25 mins at 1200×g without brake. After centrifugation the cloudy interface or buffy coat was transferred into a 50 ml tube, washed with PBS and centrifuged again for 10 minutes at 260 g. Residual erythrocytes were lysed using BD Pharm Lyse™ according to the manufacturer's protocol. Isolated PBMCs were resuspended in RPMI (10% FCS).

The binding of BT-063 (variant hVH26/hVL7) on human PBMC was determined by FACS analysis using the Zenon labeling Kit (Invitrogen). The antibodies were labeled using the anti-human IgG AlexaFluor488-Zenon kit according to manufacturer's instructions. The reagents in the kit label BT-063 via binding of fluorescently labeled Fab-fragments without affecting its antigen recognition properties. A human IgG1 anti-CD4 Antibody (BT061, Biotest), labeled in parallel with the Zenon Kit was used as positive control.

The fluorescent Fab-fragments are incubated in excess with the antibodies and bind to the Fc part of the mAb. The remaining free Fab-fragments are blocked in a second reaction with an irrelevant IgG to inhibit false positive binding. The mixture including fluorescently labeled BT-063 or BT061 was then used for staining experiments. As a negative control the reaction was performed without antibody.

1 μg of primary antibody (BT-063, α-CD4 or PBS as negative-control) was labeled with 5 μl of Zenon-AF488 reagent (AF-488 labeled anti-human IgG Fab fragments) for 5 min in a total volume of 6 μl. Then an incubation with 5 μl of the blocking reagent (irrelevant human IgG) was performed for 20 min. The whole mixture was diluted in PBS to yield proper antibody concentrations and staining of cells was performed immediately.

Example results are shown in FIG. 6. Labeled BT-063 was used in concentrations of 25, 2.5, 0.25 and 0.025 μg/ml without showing binding on human PBMC. With the anti-CD4 antibody the expected binding on human PBMC was detected, while BT-063 was not showing any binding on lymphocytes or monocytes up to concentrations of 25 μg/ml. It can therefore be concluded that BT-063 exhibits no detectable cross-reactivity to peripheral blood mononuclear cells of human origin.

The results demonstrate that the BT-063 antibody does not bind to PBMCs and therefore BT-063 binds only to soluble IL-10.

Example 6

X-Ray Crystallography 6.1 Crystallisation of BT-063 Fab in Complex with Human IL-10

Several constructs of IL-10 were designed according to published structural data (Zdanov et al., Structure, Vol. 3, 1995, pp. 591) and cloned by standard procedures into vectors for heterologous expression in *E. coli*. Test expressions of the cloned constructs were performed according to standard protocols and showed a high over-expression for IL-10 as indicated by an increase in a band in the expected range of around 18 kDa.

IL-10 protein expressed under optimised conditions yielded viable amounts for subsequent protein purification. After refolding, the protein was purified by immobilised affinity chromatography, size exclusion chromatography and ion exchange chromatography to yield protein with over 95% homogeneity as judged by Coomassie-stained SDS-PAGE. The yield of purified protein was approximately 0.3 mg per liter expression culture, which was sufficient for crystallisation trials.

The Fab fragment of BT-063 (variant hVH26/hVL7) was cleaved from the intact antibody using the protease papain and purified by protein A. Subsequently the Fab fragment was further purified by size exclusion chromatography.

The IL-10:BT-063 Fab complex was formed by mixing the purified proteins, with a molar excess of IL-10 and further purification by size exclusion chromatography. The retention volume was consistent with the size of the complex. The protein was subsequently concentrated to concentrations suitable for crystallisation.

Crystals of the IL-10:BT-063 Fab complex were prepared by the method of co-crystallisation.

6.2 Data Collection and Processing

Crystals were flash-frozen and measured at a temperature of 100 K. The X-ray diffraction data have been collected from co-crystals of IL-10 with the Fab fragment of BT-063 at the SWISS LIGHT SOURCE (SLS, Villigen, Switzerland) using cryogenic conditions.

The crystals belong to space group P6 with two complexes in the asymmetric unit. Data were processed using the programmes XDS and XSCALE. Data collection statistics are summarised in

TABLE 6

Statistics of data collection and processing

| Complex | IL-10:BT-063 |
|---|---|
| X-ray source | PX (SLS[1]) |
| Wavelength [Å] | 1.0007 |
| Detector | PILATUS |
| Temperature [K] | 100 |
| Space group | P 6 |
| Cell: a; b; c [Å] | 219.00; 219.00; 64.36 |
| α; β; γ [°] | 90.0; 90.0; 120.0 |
| Resolution [Å] [2] | 3.48 (3.72-3.48) |
| Unique reflections [2] | 21124 (3817) |
| Multiplicity [2] | 3.0 (2.9) |
| Completeness [%] [2] | 91.2 (92.3) |
| $R_{sym}$ [%] [2, 3] | 10.5 (44.0) |
| $R_{meas}$ [%] [2, 4] | 14.8 (62.2) |
| I/σ I [2] | 6.1 (1.7) |
| mean(I)/sigma [2,5] | 7.0 (1.7) |

[1] SWISS LIGHT SOURCE (SLS, Villigen, Switzerland)
[2] Numbers in brackets correspond to the highest resolution bin.

$$^3 R_{sym} = \frac{\sum_h \sum_i^{n_h} |\hat{I}_h - I_{h,i}|}{\sum_h \sum_i^{n_h} I_{h,i}} \text{ with } \hat{I}_h = \frac{1}{n_h} \sum_i^{n_h} I_{h,i}$$

where $I_{h,i}$ is the intensity value of the ith measurement of h $$^4 R_{meas} = \frac{\sum_h \sqrt{\frac{n_h}{n_h - 1}} \sum_i^{n_h} |\hat{I}_h - I_{h,i}|}{\sum_h \sum_i^{n_h} I_{h,i}} \text{ with } \hat{I}_h = \frac{1}{n_h} \sum_i^{n_h} I_{h,i}$$

where $I_{h,i}$ is the intensity value of the ith measurement of h
[5] Calculated from independent reflections 6.3 Structure Modelling and Refinement The phase information necessary to determine and analyse the structure was obtained by molecular replacement. Published models of IL-10 and a Fab fragment were used as a search model. Subsequent model building and refinement was performed according to standard protocols with the software packages CCP4 and COOT. For the calculation of the free R-factor, a measure to cross-validate the correctness of the final model, 4.2% of measured reflections were excluded from the refinement procedure (see Table 7).

The nanobody parameterisation was carried out with the programme CHEMSKETCH. LIBCHECK (CCP4) was used for generation of the corresponding library files.

The water model was built with the "Find waters . . . "-algorithm of COOT by putting water molecules in peaks of the Fo-Fc map contoured at 3.0 σ followed by refinement with REFMAC5 and checking all waters with the validation tool of COOT. The criteria for the list of suspicious waters were: B-factor greater 80, 2Fo-Fc map less than 1.2 σ, distance to closest contact less than 2.3 Å or more than 3.5 Å. The suspicious water molecules and those in the active site (distance to inhibitor less than 10 Å) were checked manually. The occupancy of side chains, which were in negative peaks in the Fo-Fc map (contoured at −3.0 σ), were set to zero and subsequently to 0.5 if a positive peak occurred after the next refinement cycle.

The Ramachandran Plot of the final model shows 80.8% of all residues in the most favoured region, 17.9% in the additionally allowed region, 0.7% of the residues in the generously allowed. Residues Val86(A), His14(B), Asp86

(B), Ser131(C), Val56(D) and Val56(F) are found in the disallowed region of the Ramachandran plot (Table 7). They are either confirmed by the electron density map or could not be modelled in another sensible conformation. Statistics of the final structure and the refinement process are listed in Table 7.

TABLE 7

| Refinement statistics [1] | |
|---|---|
| Complex | IL-10:BT-063 |
| Resolution [Å] | 20.0-3.48 |
| Number of reflections (working/test) | 20199/889 |
| $R_{cryst}$ [%] | 29.7 |
| $R_{free}^2$ [%] | 35.5 |
| Total number of atoms: | |
| Protein | 8870 |
| Water | |
| Ligand | — |
| Deviation from ideal geometry: [3] | |
| Bond lengths [Å] | 0.007 |
| Bond angles [°] | 0.93 |
| Bonded B's [4] [Å$^2$] | 0.0 |
| Ramachandran Plot: [5] | |
| Most favoured regions | 80.8 |
| Additional allowed regions | 17.9 |
| Generously allowed regions | 0.7 |
| Disallowed regions | 0.6 |

[1] Values as defined in REFMAC5, without sigma cut-off
[2] Test-set contains 4.2% of measured reflections
[3] Root mean square deviations from geometric target values
[4] Calculated with programme MOLEMAN
[5] Calculated with programme PROCHECK 6.4 X-ray structure analysis The complex structure of human IL-10 bound by BT-063 Fab antibody fragment was analysed at a resolution of 3.48 Å and reveals the detailed binding mode of the Fab antibody fragment.

The resulting electron density shows an unambiguous binding mode for the Fab fragment, including the orientation and conformation of the Fab fragment. The crystal of space group P6 contains two complexes in the asymmetric unit.

The structure of IL-10 in complex with Fab is represented in FIG. 7. Two Fab fragments bind with their CDR loops to each homodimer of IL-10.

The following residues of IL-10 (molecules A and B) can be found in the vicinity of the CDR loops within a maximum distance of 3.9 Å: Arg27, Lys 34, Gln38, Met39, Asp41, Gln42, Asp44, Leu46, Glu50, Leu53, Glu142, Asp144, Ile145, Asn148, Tyr149, Glu151, and Thr155.

The following residues of the CDR loops can be found in the vicinity of the IL-10 within a maximum distance of 3.9 Å: Phe27, Ser28, Ala30, Thr31, Tyr32, Trp52, Arg53, Gly54, Ser56, Asn73, Ser74, Tyr100, Gly101, Tyr103 (molecules C and E), Ser32, Asn33, Asn35, Tyr37, Lys55 (molecules D and F).

The binding site of BT-063 coincides with the binding site of the IL-10 receptor on the surface of IL-10 as shown by overlaying the complex structure of IL-10:BT-063 with a published structure of the IL-10:IL-10R1 receptor complex (FIG. 8).

The BT-063 amino acid residues in contact with human IL-10 as identified by X-ray analysis are highlighted on the linear amino acid sequence of BT-063 variable antibody domains shown below.

```
BT-063 VL
                                           (SEQ ID No: 69)
DVVMTQSPLS LPVTLGQPAS ISCRSSQNIV HSNGNTYLEW

YLQRPGQSPR LLIYKVSNRF SGVPDRFSGS GSGTDFTLKI

SRVEAEDVGV YYCFQGSHVP WTFGQGTKVE IK

BT-063 VH:
                                           (SEQ ID No: 70)
EVQLVESGGG LVQPGGSLRL SCAASGFSFA TYGVHWVRQS

PGKGLEWLGV IWRGGSTDYS AAFMSRLTIS KDNSKNTVYL

QMNSLRAEDT AVYFCAKQAY GHYMDYWGQG TSVTVSS
```

CDR regions (Honegger and Plückthun (2001) J. Mol. Biol., 309, 657-670) are underlined (CDR1, CDR2 and CDR3 of the light chain are SEQ ID Nos: 71, 72 and 73, respectively; CDR1, CDR2 and CDR3 of the heavy chain are SEQ ID Nos: 74, 75 and 76, respectively). Contact residues with IL-10 are shown in bold.

Within the light chain contact residues are found in CDR1 and CDR2 but not in CDR3. Regarding the heavy chain resides of all three CDRs are involved in antigen binding. Two residues of FR3 (Asn73 and Ser74) also contribute to antigen binding.

Ser28 and Ala30 at the beginning of CDR1 are part of the murine VH predecessor sequence (BN-10) and not present in the selected human framework (3-66*04). Both positions are less frequently involved in antigen binding and were introduced as alternative amino acids during the humanisation process.

Residues Asn73 and Ser74 are found in murine and frequently in human antibody framework sequences but are usually not involved in antigen binding. (www.bioc.uzh.ch/antibody; Honegger and Plückthun, 2001). Their contribution to antigen binding is unexpected.

IL-10 amino acid residues involved in BT-063 binding are shown below. Also indicated are residues of IL-10 involved in binding to the high affinity IL-10 receptor chain (IL-10R1) and the low affinity receptor chain (IL-10R2). Both receptor chains are involved in the binding of a IL-10 homodimer and necessary for signaling. In sequence A the residues which contact BT-063 are shown in bold and are underlined. In sequence B the contact residues to IL-10R1 are marked in bold and underlined, contact residues to IL-10R2 are marked in italics and underlined and contact residues shared by IL-10R1 and 2 are marked in as being in bold, italics and underlined (Pletnev et al 2005).

```
A
                                           (SEQ ID NO: 1)
SPGQGTQSEN SCTHFPGNLP NMLRDLRDAF SRVKTFFQMK

DQLDNLLLKE SLLEDFKGYL GCQALSEMIQ FYLEEVMPQA

ENQDPDIKAH VNSLGENLKT LRLRLRRCHR FLPCENKSKA

VEQVKNAFNK LQEKGIYKAM SEFDIFINYI EAYMTMKIRN

B
                                           (SEQ ID NO: 1)
SPGQGTQSEN SCTHFPGNLP NMLRDLRDAF SRVKTFFQMK

DQLDNLLLKE SLLEDFKGYL GCQALSEMIQ FYLEEVMPQA

ENQDPDIKAH VNSLGENLKT LRLRLRRCHR FLPCENKSKA

VEQVKNAFNK LQEKGIYKAM SEFDIFINYI EAYMTMKIRN
```

It can be seen that BT-063 binds to a discontinuous epitope of IL-10 comprising residues of helix A (Arg27, Lys34, Gln38, Met39, Asp41) and the N-terminal part of helix B (Glu50 and Leu53) including the connecting loop sequence (Glu42, Asp44, Leu46) of one IL-10 monomer as well as residues of the helix F' (Glu142, Asp144, Ile145, Asn148, Tyr149, Glu151, Thr155) of the second IL-10 monomer.

As such, it can be seen that BT-063 is blocking the binding site of the high affinity receptor chain IL-10R1.

Example 7

In Vivo Single Dose Toxicity Study in Cynomolgous Monkey

A single dose toxicity study including safety pharmacology parameters was performed in Cynomolgus monkeys following a single intravenous injection of BT-063 (variant hVH26/hVL7). Animals were distributed into four groups (placebo, 1 mg/kg, 7 mg/kg and 50 mg/kg) with 4 animals/sex/group. BT-063 was intravenously injected on day 1. Half of the animals were necropsied after 5 days, while the remaining animals were sacrificed on day 28.

The low dose level of 1 mg/kg in this study corresponds to a human equivalent dose of ~300 μg/kg, resulting in a total human dose of 18 mg (60 kg body weight). A similar dose of the BT-063 predecessor antibody B-N10 had been applied daily for 21 days in a small investigator initiated trial (Llorente, 2000). This amount of antibody has shown pharmacological effects and clinical efficacy. The low dose level was therefore chosen accordingly. The high dose was chosen as a multiple (50) of the starting dose. The intermediate dose is the geometric mean of the low and the high doses.

During the study no toxicologically significant or relevant changes in physiological or histopathology parameters were observed. In addition, changes in clinical chemistry parameters were considered of little or no toxicological significance.

Example 8

Estimated Target Occupancy by the IL-10 Specific BT-063 Antibody after Intravenous Administration In order to estimate the neutralization of IL-10 in human healthy volunteers after a single intravenous injection of the mAb BT-063, the target occupancy of IL-10 by BT-063 (variant hVH26/hVL7) in a healthy volunteer was estimated based on the dissociation constant of the BT-063-IL-10 complex and on standard parameters for human blood volumes and the assumption that BT-063 distributes solely within the blood stream.

8.1 Method

Unvalidate Microsoft-Excel-Software was used to calculate and display the dose dependent target occupancy of IL-10 by BT063.

Assumptions for calculations:
Blood volume (serum): 3.5 l
Mean concentration of IL-10 in healthy volunteer serum: 15 pg/ml
$k_D$ (dissociation constant, BT063<->IL-10): 3 nM (derived from Biacore studies)
molecular weight IL-10 dimer: 37 000 g/mol
molecular weight BT063: 150 000 g/mol Using the law of mass action a target occupancy of IL-10 at different doses of the BT-063 antibody was calculated. For the theoretical calculations of free and complexed IL-10 it was assumed that one molecule of an anti-IL10 antibody binds to one dimer of IL-10. The following equilibrium equation was applied:

Law of mass action: BT063+IL10⇌BT063/IL-10 complex

A resulting dissociation constant is determined by steady state concentrations of BT063 ([BT063]), IL-10 ([IL-10]) and the BT063-IL-10 complex ([complex]):

$$k_D = \frac{[BT063]*[IL-10]}{[complex]}$$

Steady state concentrations are not directly available, but can be calculated from starting concentrations of $[BT063_0]$ and $[IL-10_0]$ and the steady state concentration of the complex ([complex]):

$$[BT063]=[BT063_0]-[complex]$$

$$[IL-10]=[IL-10_0]-[complex]$$

For calculation of IL-10 occupancy by BT063 after intravenous injection of the mAb, the following assumptions were made:

BT063 distributes equally and exclusively in the blood directly after injection

BT063 molecules do not leave the blood volume

IL-10 is exclusively distributed in the blood and there are no other sources of IL-10

TL-10 molecules or BT063-IL-10 complexes do not leave the blood stream and are not drawn away from circulation by Fc-receptor mediated or other mechanisms the equilibrium is reached rapidly These assumptions are artificially chosen and do not represent the probable biologically relevant situation in vivo. It can be assumed that the BT063 distribution volume is larger than estimated, since BT063 most probably distributes additionally to extravasal compartments of the body, leading to rapidly diminished concentrations of the mAb in the circulation. Furthermore, it can be expected that extravasal sources exist for IL-10 and the amount of IL-10 present in the body is higher than that estimated here.

Conclusively, the calculations made here overestimate the percentage of complexed IL-10 in vivo. The estimated complexing of IL-10 thus will not be reached in vivo and a safety margin for the calculated values exist.

As a calculation basis, the following constants were used:
molecular weight (BT063): 150 000 g/mol
molecular weight (IL-10 dimer): 37 000 g/mol
mean concentration of IL-10 in healthy volunteer serum: 15 pg/ml
blood serum volume: 3.5 l On this basis the dose dependent percentage of IL-10 that is complexed by BT063 under equilibrium concentrations can be computed. Table 8 and FIG. 10 show the dose dependency of IL-10 blockade by BT063 after intravenous injection of the mAb.

TABLE 8

Calculation of IL-10 occupancy by BT-063 with increasing total dose of BT-063 injected intravenously.

| BT063 total dose (μg) | % IL-10 complexed by BT063 |
|---|---|
| 1.75 | 0.1 |
| 5.25 | 0.3 |
| 16 | 1.0 |
| 47 | 2.9 |
| 142 | 8.3 |
| 175* | 10.0 |
| 425 | 21.3 |
| 750* | 32.3 |
| 1,276 | 44.7 |
| 3,827 | 70.8 |
| 3,500* | 69.0 |
| 7,500* | 82.6 |
| 11,482 | 87.9 |
| 15,000* | 90.5 |
| 30,000* | 95.0 |
| 34,445 | 95.6 |
| 60,000* | 97.4 |
| 100,000* | 98.5 |
| 103,336 | 98.5 |
| 310,007 | 99.5 |
| 930,022 | 99.8 |
| 2,790,065 | 99.9 |

(*Doses that are intended to be applied in the healthy volunteer clinical trial are marked in grey).

To theoretically estimate the influences of different IL-10 concentrations or a different affinity (dissociation constant) of BT-063 to IL-10, the corresponding curves were compared to the original dose-response dependency depicted in FIG. 10.

FIG. 11 shows that the percentage of complexed IL-10 is merely independent of IL-10 levels in the blood. Even 1000 fold changes in IL-10 levels have only marginal impact on the dose-response curve. Therefore fluctuations in IL-10 concentrations do not alter the occupancy of IL-10 by BT-063 on a percent basis.

Although, the affinity of BT-063 to human IL-10 is known from Biacore studies, other methods might lead to a slightly different dissociation constant for the complex (Waibler ct al., J Allergy Clin Immunol., 2008 November; 122(5): 890-2, Epub 2008, September 20). It was therefore analyzed to what degree a different affinity would alter the dose-response of IL-10 occupancy.

In contrast, to altered IL-10 levels different affinities of BT-063 to IL-10 shift the curves to a higher occupancy of BT-063 for the case of a higher affinity (10 times higher) or vice versa for lower affinities (FIG. 12).

From the data it can be concluded that 175 μg BT-063 (the intended starting dose of the first healthy volunteer human clinical trial) is able to neutralize about 10% of all present IL-10 in the blood of a healthy volunteer. Up to a dose of 10 mg BT-063 there is a log linear relationship between the dose of BT-063 and the percentage of complexed IL-10. With 10 mg BT-063 about 85% of all IL-10 will be neutralized.

The course of the calculated curve is largely independent of IL-10 concentration in the blood, meaning that the neutralizing capacity of BT-063 (on a percent basis) will be influenced by different IL-10 levels only to a minor extent. Therefore, it can be assumed that the curve presented for healthy volunteers will additionally apply for systemic lupus erythematosus (SLE) patients who bear increased IL-10 levels in the blood. From these data it can be concluded that doses above 175 μg total dose BT-063 in healthy volunteers will neutralize more than 10% of the cytokine. Above this dose and up to 10 mg total dose the complexing of IL-10 by the mAb will yield a log linear relationship up to 85%. Above 10 mg BT-063, the curve runs into saturation levels. Nearly 100% neutralization are reached at 100 mg total dose.

Example 8

In Vivo Single Dose Toxicity Study in Healthy Volunteers

A study was conducted to monitor the safety and tolerability of BT-063 (variant hVH26/hVL7), and the effects of BT-063 administration, using escalating doses of the antibody in healthy volunteers.

Twenty-three volunteers received a single intravenous administration of BT-063, in 8 dosage groups. The dosage groups were as follows: 0.175 mg, 0.75 mg, 3.5 mg, 7 mg, 15 mg, 30 mg, 60 mg and 100 mg. There were three volunteers per group, except for the 100 mg dose group where there were two volunteers.

Each dose is diluted with 0.9% sodium chloride injection up to a total volume of 20 ml. The dose is administered as a single continuous intravenous infusion using an infusion pump over 2 hours.

The volunteers were assessed over a period of 85 days after the injection and blood was taken at multiple time points over this period.

From the blood taken assessments were made on the levels of cytokines IFNγ, IL-1β, IL-2, IL-4, IL-5, IL-6, IL-8, IL-10 and TNFα.

Results

A non-dose dependent transient increase of IL-6 and IL-8 was present within the 24 hours post infusion, returning to pre-dose levels after 3 days. This effect is thought to be associated with the infusion event rather than with the antibody since there was no dose relationship and the effect occurred even at the lowest dose.

Surprisingly, given that IL-10 is an important regulatory cytokine, no increase in levels of IFNγ, IL-1β, IL-2, IL-4, IL-5, and TNFα were detected, as shown in FIG. 13. The lack of elevation in levels of IL-4, IL-5 IFN-γ, IL-2 also confirm that there is no T-helper cell activation resulting from the BT-063 administration. Further, since body temperature is also an indication of the large-scale release of pro-inflammatory cytokines, this parameter was also measured in the treated volunteers. However, no increase in body temperature was detected after administration.

As shown in FIG. 14, IL-10 plasma concentration is influenced by administration of BT-063, with detected plasma IL-10 increasing as the dose of BT-063 is increased. It is noted that the assay used detects both free IL-10 and IL-10 bound to BT-063. There are two possible explanations for the increase: (1) a prolonged half life of IL-10, with binding of IL-10 to BT-063 preventing IL-10 internalization, and concomitantly no elimination of IL-10 from the blood (there is normally a rapid turnover of IL-10, with the half life of secreted IL-10 being approximately 2.3-3.5 hours (Huhn et al., Blood (1996) January 15: 87(2): 699-705)); and/or (2) induction of a negative feedback loop—with BT-063 blocking the binding of IL-10 to its receptor no cellular uptake of IL-10 is possible, triggering B-cells to produce more IL-10. We consider that scenario (2) is more probable since it is confirmed by in vitro data taken from whole blood culture experiments with BT-063 and murine IL-1 OR knockout cells (Mahnke et al., unpublished data).

Pharmacokinetics

The pharmacokinetic data showed that the Cmax, AUC and half-life of BT-063 are in the range of the expected theoretical values. The terminal half-life of BT-063 being between 15 and 30 days. After administration of doses of 30 mg or higher, BT-063 is still detectable in the plasma after 85 days.

No human anti-human antibodies (HAHA) were observed in the treated volunteers, despite the fact that HAHA responses have been observed with other cytokine neutralizing antibodies (e.g. with Adalimumab, a humanized anti-TNF alpha).

Despite the increase in detected amounts of IL-10 after administration of BT-063 it is noted that this study demonstrates the safety and tolerability of even large dosages of BT-063 and thus it can be concluded that sufficient dosages of BT-063 can be safely administered to SLE patients to counteract the effects of excess IL-10.

The invention claimed is:

1. A method of detecting the level of soluble IL-10 homodimer in a sample, comprising: (a) contacting a sample with an antibody or fragment thereof; and (b) determining the amount of IL-10 present in the sample by determining the amount of antibody or fragment thereof bound to IL-10; wherein the antibody or fragment thereof is a humanized antibody or fragment thereof that binds to IL-10 in homodimeric form by binding a discontinuous epitope comprising residues of both monomers, and wherein said antibody or fragment thereof comprises a variable light chain comprising the amino acid sequences of CDR1, CDR2 and CDR3 of SEQ ID NO: 2, and a variable heavy chain comprising the amino acid sequences of CDR1, CDR2 and CDR3 of SEQ ID NO: 3, wherein the variable heavy chain further comprises the residues Asn73 and Ser74 of SEQ ID NO:70 which contact IL-10 when said antibody binds to IL-10.

2. The method of claim 1, wherein the sample is a plasma sample.

3. The method of claim 1, wherein the antibody or fragment thereof is labeled.

4. The method of claim 3, wherein the step of determining the amount of antibody or fragment thereof bound to IL-10 comprises determining the amount of label present.

5. The method of claim 1, wherein said antibody or fragment thereof binds to a discontinuous epitope comprising residues of helix A of one IL-10 monomer and residues of helix F' of the other IL-10 monomer.

6. The method of claim 1, wherein said antibody or fragment thereof binds to the same region of IL-10 as the IL-10 receptor α (IL-10Rα) and is not capable of binding IL-10 when the IL-10 is bound to the IL-10 receptor.

7. The method of claim 1, wherein said antibody or fragment thereof comprises the variable heavy chain sequence of SEQ ID NO: 70 and the variable light chain sequence of SEQ ID NO: 69.

8. The method of claim 1, wherein said antibody or fragment thereof does not bind to the same region of IL-10 as the IL-10 receptor β (IL-10Rβ).

9. The method of claim 1, wherein said antibody or fragment thereof binds to a discontinuous epitope comprising residues of helix A of one IL-10 monomer and residues of helix F' of the other IL-10 monomer of an IL-10 homodimer.

10. The method of claim 1, wherein the residues of the discontinuous epitope are within the first 55 amino acids of one monomer and within the last 20 amino acids of the other monomer of an IL-10 homodimer.

11. The method of claim 10, wherein the residues of the discontinuous epitope are within the amino acids of 20 to 55 of one IL-10 monomer and with the last 20 amino acids of the other IL-10 monomer of said IL-10 homodimer.

12. The method of claim 1, wherein said antibody or fragment thereof does not induce antibody-dependent cell-mediated cytotoxicity and/or complement-dependent cytotoxicity.

13. The method of claim 1, wherein said antibody or fragment thereof is capable of preventing IL-10 signaling through IL-10 receptor α.

14. A method of detecting the level of soluble IL-10 in a sample, comprising: (a) contacting a sample with an antibody or fragment thereof; and (b) determining the amount of IL-10 present in the sample by determining the amount of antibody or fragment thereof bound to IL-10; wherein the antibody or fragment thereof is a humanized antibody or fragment thereof which comprises a variable light chain comprising the amino acid sequences of CDR1, CDR2 and CDR3 of SEQ ID NO: 2, and a variable heavy chain comprising the amino acid sequences of CDR1, CDR2 and CDR3 of SEQ ID NO: 3, wherein the variable heavy chain further comprises the residues Asn73 and Ser74 of SEQ ID NO:70 which contact IL-10 when said antibody binds to IL-10.

\* \* \* \* \*

SEQUENCE LISTING

```
<160> NUMBER OF SEQ ID NOS: 76

<210> SEQ ID NO 1
<211> LENGTH: 160
<212> TYPE: PRT
<213> ORGANISM: Human

<400> SEQUENCE: 1

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 2
<211> LENGTH: 114
<212> TYPE: PRT
<213> ORGANISM: Mus musculus

<400> SEQUENCE: 2

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Thr Arg Leu Glu Ala Glu Asp Leu Gly Val Tyr Tyr Cys Phe Gln Gly
                    85                  90                  95
Ser His Val Pro Trp Thr Phe Gly Gly Gly Thr Lys Leu Glu Ile Lys
                100                 105                 110
Arg Ala

<210> SEQ ID NO 3
<211> LENGTH: 116
<212> TYPE: PRT
<213> ORGANISM: Mus musculus

<400> SEQUENCE: 3

Gln Val Gln Leu Lys Gln Ser Gly Pro Gly Leu Leu Gln Pro Ser Gln
1               5                   10                  15
Ser Leu Ser Ile Ser Cys Thr Val Ser Gly Phe Ser Leu Ala Thr Tyr
                20                  25                  30
Gly Val His Trp Val Arg Gln Ser Pro Gly Lys Gly Leu Glu Trp Leu
                35                  40                  45
Gly Val Ile Trp Arg Gly Gly Ser Thr Asp Tyr Ser Ala Ala Phe Met
                50                  55                  60
Ser Arg Leu Ser Ile Thr Lys Asp Asn Ser Lys Ser Gln Val Phe Phe
65                  70                  75                  80
Lys Met Asn Ser Leu Gln Ala Asp Asp Thr Ala Ile Tyr Phe Cys Ala
                85                  90                  95
Lys Gln Ala Tyr Gly His Tyr Met Asp Tyr Trp Gly Gln Gly Thr Ser
                100                 105                 110
Val Thr Val Ser
        115

<210> SEQ ID NO 4
<211> LENGTH: 16
<212> TYPE: PRT
<213> ORGANISM: Mus musculus

<400> SEQUENCE: 4

Arg Ser Ser Gln Asn Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Val Pro Trp Thr
1               5

<210> SEQ ID NO 7
<211> LENGTH: 5
<212> TYPE: PRT
```

<213> ORGANISM: Mus musculus

<400> SEQUENCE: 7

Thr Tyr Gly Val His
1               5

<210> SEQ ID NO 8
<211> LENGTH: 16
<212> TYPE: PRT
<213> ORGANISM: Mus musculus

<400> SEQUENCE: 8

Val Ile Trp Arg Gly Gly Ser Thr Asp Tyr Ser Ala Ala Phe Met Ser
1               5                   10                  15

<210> SEQ ID NO 9
<211> LENGTH: 9
<212> TYPE: PRT
<213> ORGANISM: Mus musculus

<400> SEQUENCE: 9

Gln Ala Tyr Gly His Tyr Met Asp Tyr
1               5

<210> SEQ ID NO 10
<211> LENGTH: 342
<212> TYPE: DNA
<213> ORGANISM: Mus musculus

<400> SEQUENCE: 10
gatgttttga tgacccaaac tccactctcc ctgcctgtca gtcttggaga tcaagcctcc      60
atctcttgca gatctagtca gaacattgta catagtaatg aaacacccta tttagaatgg     120
tacctgcaga accaggcca gtctccaaag ctcctgatct acaaagtttc caaccgattt     180
tctggggtcc cagacaggtt cagtggcagt ggatcaggga cagatttcac actcaagatc     240
accagattgg aggctgagga tctgggagtt tattactgct ttcaaggttc acatgttccg     300
tggacgttcg gtggaggcac caagctggaa atcaaacggg cc                        342

<210> SEQ ID NO 11
<211> LENGTH: 348
<212> TYPE: DNA
<213> ORGANISM: Mus musculus

<400> SEQUENCE: 11
caggtgcagc tgaagcagtc aggacctggc ctactgcagc cctcacagag cctgtccata      60
tcctgcacag tctctggttt ctcattagct acctatggtg tacactgggt tcgccagtct     120
ccaggaaagg gtctggagtg gctgggagtg atttggagag tgggagcac agactacagt     180
gcagctttca tgtccagact gagcatcacc aaggacaact ccaagagcca gttttctttt     240
aaaatgaaca gtctgcaagc tgatgacact gccatttact ctgtgccaa acaggcgtat     300
ggtcactaca tggactactg gggtcaagga acctcagtca ccgtctcc                  348

<210> SEQ ID NO 12
<211> LENGTH: 112
<212> TYPE: PRT
<213> ORGANISM: Mus musculus

<400> SEQUENCE: 12

Asp Val Leu Met Thr Gln Thr Pro Leu Ser Leu Pro Val Ser Leu Gly
1               5                   10                  15

```
Asp Gln Ala Ser Ile Ser Cys Arg Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Leu Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 13
<211> LENGTH: 117
<212> TYPE: PRT
<213> ORGANISM: Mus musculus

<400> SEQUENCE: 13

```
Gln Val Gln Leu Lys Gln Ser Gly Pro Gly Leu Leu Gln Pro Ser Gln
1               5                   10                  15

Ser Leu Ser Ile Ser Cys Thr Val Ser Gly Phe Ser Leu Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115
```

<210> SEQ ID NO 14
<211> LENGTH: 100
<212> TYPE: PRT
<213> ORGANISM: Human

<400> SEQUENCE: 14

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
        100
```

<210> SEQ ID NO 15
<211> LENGTH: 12
<212> TYPE: PRT
<213> ORGANISM: Human

<400> SEQUENCE: 15

Trp Thr Phe Gly Gln Gly Thr Lys Val Glu Ile Lys
1               5                   10

<210> SEQ ID NO 16
<211> LENGTH: 97
<212> TYPE: PRT
<213> ORGANISM: Human

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 17
<211> LENGTH: 15
<212> TYPE: PRT
<213> ORGANISM: Human

<400> SEQUENCE: 17

Tyr Phe Asp Tyr Trp Gly Gln Gly Thr Leu Val Thr Val Ser Ser
1               5                   10                  15

<210> SEQ ID NO 18
<211> LENGTH: 112
<212> TYPE: PRT
<213> ORGANISM: Artificial Sequence
<220> FEATURE:
<223> OTHER INFORMATION: hVL1

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

```
Ser His Val Pro Trp Thr Phe Gly Gln Gly Thr Lys Val Glu Ile Lys
            100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: hVL2

<400> SEQUENCE: 19

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 20
<211> LENGTH: 112
<212> TYPE: PRT
<213> ORGANISM: Artificial Sequence
<220> FEATURE:
<223> OTHER INFORMATION: hVL3

<400> SEQUENCE: 20

```
Asp Val Val Met Thr Gln Thr Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 21
<211> LENGTH: 112
<212> TYPE: PRT
<213> ORGANISM: Artificial Sequence
<220> FEATURE:
<223> OTHER INFORMATION: hVL4

<400> SEQUENCE: 21

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
```

```
                    20                  25                  30

Asn Gly Asn Thr Tyr Leu Glu Trp Tyr Leu Gln Arg Pro Gly Gln Ser
                35                  40                  45

Pro Arg Arg Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: hVL5

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
                20                  25                  30

Asn Gly Asn Thr Tyr Leu Glu Trp Phe Gln Gln Arg Pro Gly Gln Ser
                35                  40                  45

Pro Arg Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: hVL6

<400> SEQUENCE: 23

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
                20                  25                  30

Asn Gly Asn Thr Tyr Leu Glu Trp Phe Gln Gln Arg Pro Gly Gln Ser
                35                  40                  45

Pro Arg Arg Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 24
<211> LENGTH: 112
<212> TYPE: PRT
<213> ORGANISM: Artificial Sequence
<220> FEATURE:
<223> OTHER INFORMATION: hVL7

<400> SEQUENCE: 24

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 25
<211> LENGTH: 112
<212> TYPE: PRT
<213> ORGANISM: Artificial Sequence
<220> FEATURE:
<223> OTHER INFORMATION: hVL8

<400> SEQUENCE: 25

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: hVL9

<400> SEQUENCE: 26

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asn Gly Asn Thr Tyr Leu Glu Trp Tyr Leu Gln Arg Pro Gly Gln Ser
```

35                  40                  45

Pro Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110

<210> SEQ ID NO 27
<211> LENGTH: 112
<212> TYPE: PRT
<213> ORGANISM: Artificial Sequence
<220> FEATURE:
<223> OTHER INFORMATION: hVL10

<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
                20                  25                  30

Asn Gly Asn Thr Tyr Leu Glu Trp Tyr Leu Gln Arg Pro Gly Gln Ser
            35                  40                  45

Pro Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110

<210> SEQ ID NO 28
<211> LENGTH: 112
<212> TYPE: PRT
<213> ORGANISM: Artificial Sequence
<220> FEATURE:
<223> OTHER INFORMATION: hVL11

<400> SEQUENCE: 28

Asp Val Val Met Thr Gln Thr Pro Leu Ser Leu Pro Val Thr Leu Gly
1               5                   10                  15

Gln Pro Ala Ser Ile Ser Cys Arg Ser Ser Gln Asn Ile Val His Ser
                20                  25                  30

Asn Gly Asn Thr Tyr Leu Glu Trp Tyr Leu Gln Arg Pro Gly Gln Ser
            35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110

<210> SEQ ID NO 29
<211> LENGTH: 112

<212> TYPE: PRT
<213> ORGANISM: Artificial Sequence
<220> FEATURE:
<223> OTHER INFORMATION: hVL12

<400> SEQUENCE: 29

Asp Val Val Met Thr Gln Thr Pro Leu Ser Leu Pro Val Thr Leu Gly
1               5                   10                  15

Gln Pro Ala Ser Ile Ser Cys Arg Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 30
<211> LENGTH: 117
<212> TYPE: PRT
<213> ORGANISM: Artificial Sequence
<220> FEATURE:
<223> OTHER INFORMATION: hVH1

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: hVH2

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ala Pro Gly Lys Gly Leu Glu Trp Val

```
            35                  40                  45
Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 32
<211> LENGTH: 117
<212> TYPE: PRT
<213> ORGANISM: Artificial Sequence
<220> FEATURE:
<223> OTHER INFORMATION: hVH3

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ser Pro Gly Lys Gly Leu Glu Trp Val
        35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 33
<211> LENGTH: 117
<212> TYPE: PRT
<213> ORGANISM: Artificial Sequence
<220> FEATURE:
<223> OTHER INFORMATION: hVH4

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Leu
        35                  40                  45

Gly Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Gln Ala Tyr Gly His Tyr Met Asp Tyr Trp Gly Gln Gly Thr Leu
                100                 105                 110

Val Thr Val Ser Ser
            115

<210> SEQ ID NO 34
<211> LENGTH: 117
<212> TYPE: PRT
<213> ORGANISM: Artificial Sequence
<220> FEATURE:
<223> OTHER INFORMATION: hVH5

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
        50                  55                  60

Ser Arg Leu Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
                100                 105                 110

Val Thr Val Ser Ser
            115

<210> SEQ ID NO 35
<211> LENGTH: 117
<212> TYPE: PRT
<213> ORGANISM: Artificial Sequence
<220> FEATURE:
<223> OTHER INFORMATION: hVH6

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
        50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
                100                 105                 110

Val Thr Val Ser Ser
            115

<210> SEQ ID NO 36
<211> LENGTH: 117
<212> TYPE: PRT
<213> ORGANISM: Artificial Sequence
```

<220> FEATURE:
<223> OTHER INFORMATION: hVH7

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: hVH8

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Phe
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
            100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: hVH9

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Phe Cys Ala
                 85                  90                  95

Lys Gln Ala Tyr Gly His Tyr Met Asp Tyr Trp Gly Gln Gly Thr Leu
            100                 105                 110

Val Thr Val Ser Ser
            115

<210> SEQ ID NO 39
<211> LENGTH: 117
<212> TYPE: PRT
<213> ORGANISM: Artificial Sequence
<220> FEATURE:
<223> OTHER INFORMATION: hVH10

<400> SEQUENCE: 39

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gln Ala Tyr Gly His Tyr Met Asp Tyr Trp Gly Gln Gly Thr Leu
            100                 105                 110

Val Thr Val Ser Ser
            115

<210> SEQ ID NO 40
<211> LENGTH: 117
<212> TYPE: PRT
<213> ORGANISM: Artificial Sequence
<220> FEATURE:
<223> OTHER INFORMATION: hVH11

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

-continued

Arg Gln Ala Tyr Gly His Tyr Met Asp Tyr Trp Gly Gln Gly Thr Ser
                100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: hVH12

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Gly Val His Trp Val Arg Gln Ala Pro Gly Lys Gly Leu Glu Trp Leu
            35                  40                  45

Gly Val Ile Trp Arg Gly Gly Ser Thr Asp Tyr Ser Ala Ala Phe Met
        50                  55                  60

Ser Arg Leu Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
                100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: hVH13

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Gly Val His Trp Val Arg Gln Ala Pro Gly Lys Gly Leu Glu Trp Val
            35                  40                  45

Ser Val Ile Trp Arg Gly Gly Ser Thr Asp Tyr Ser Ala Ala Phe Met
        50                  55                  60

Ser Arg Phe Thr Ile Ser Arg Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Leu
                100                 105                 110

Val Thr Val Ser Ser
        115

<210> SEQ ID NO 43
<211> LENGTH: 117
<212> TYPE: PRT

-continued

```
<213> ORGANISM: Artificial Sequence
<220> FEATURE:
<223> OTHER INFORMATION: hVH14

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Leu
            100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: hVH15

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: hVH16

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Gly Val His Trp Val Arg Gln Ala Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Leu
            100                 105                 110

Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: hVH17

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Val His Trp Val Arg Gln Ala Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: hVH18

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
```

```
                            85                  90                  95
Arg Gln Ala Tyr Gly His Tyr Met Asp Tyr Trp Gly Gln Gly Thr Leu
                100                 105                 110

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: hVH19

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Ser Ala Ala Phe Met
        50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
                100                 105                 110

Val Thr Val Ser Ser
        115

<210> SEQ ID NO 49
<211> LENGTH: 117
<212> TYPE: PRT
<213> ORGANISM: Artificial Sequence
<220> FEATURE:
<223> OTHER INFORMATION: hVH20

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Ser Ala Ala Phe Met
        50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
                100                 105                 110

Val Thr Val Ser Ser
        115

<210> SEQ ID NO 50
<211> LENGTH: 117
```

```
<212> TYPE: PRT
<213> ORGANISM: Artificial Sequence
<220> FEATURE:
<223> OTHER INFORMATION: hVH21

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ala Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 51
<211> LENGTH: 117
<212> TYPE: PRT
<213> ORGANISM: Artificial Sequence
<220> FEATURE:
<223> OTHER INFORMATION: hVH22

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Val
        35                  40                  45

Ser Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 52
<211> LENGTH: 117
<212> TYPE: PRT
<213> ORGANISM: Artificial Sequence
<220> FEATURE:
<223> OTHER INFORMATION: hVH23

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
```

```
                  20                  25                  30
Gly Val His Trp Val Arg Gln Ser Pro Gly Lys Gly Leu Glu Trp Leu
            35                  40                  45
Gly Val Ile Trp Arg Gly Gly Ser Thr Asp Tyr Ser Ala Ala Phe Met
        50                  55                  60
Ser Arg Phe Thr Ile Ser Lys Asp Asn Ser Lys Asn Thr Val Tyr Phe
65                  70                  75                  80
Gln Met Asn Ser Leu Arg Ala Glu Asp Thr Ala Val Tyr Phe Cys Ala
                85                  90                  95
Lys Gln Ala Tyr Gly His Tyr Met Asp Tyr Trp Gly Gln Gly Thr Ser
            100                 105                 110
Val Thr Val Ser Ser
        115

<210> SEQ ID NO 53
<211> LENGTH: 117
<212> TYPE: PRT
<213> ORGANISM: Artificial Sequence
<220> FEATURE:
<223> OTHER INFORMATION: hVH24

<400> SEQUENCE: 53

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Phe Ala Thr Tyr
            20                  25                  30
Gly Val His Trp Val Arg Gln Ser Pro Gly Lys Gly Leu Glu Trp Leu
        35                  40                  45
Gly Val Ile Trp Arg Gly Gly Ser Thr Asp Tyr Ser Ala Ala Phe Met
    50                  55                  60
Ser Arg Leu Thr Ile Ser Arg Asp Asn Ser Lys Asn Thr Val Tyr Phe
65                  70                  75                  80
Gln Met Asn Ser Leu Arg Ala Glu Asp Thr Ala Val Tyr Phe Cys Ala
                85                  90                  95
Lys Gln Ala Tyr Gly His Tyr Met Asp Tyr Trp Gly Gln Gly Thr Ser
            100                 105                 110
Val Thr Val Ser Ser
        115

<210> SEQ ID NO 54
<211> LENGTH: 117
<212> TYPE: PRT
<213> ORGANISM: Artificial Sequence
<220> FEATURE:
<223> OTHER INFORMATION: hVH25

<400> SEQUENCE: 54

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Phe Ala Thr Tyr
            20                  25                  30
Gly Val His Trp Val Arg Gln Ser Pro Gly Lys Gly Leu Glu Trp Leu
        35                  40                  45
Gly Val Ile Trp Arg Gly Gly Ser Thr Asp Tyr Ser Ala Ala Phe Met
    50                  55                  60
Ser Arg Leu Thr Ile Ser Lys Asp Asn Ser Lys Asn Thr Leu Tyr Phe
65                  70                  75                  80
```

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 55
<211> LENGTH: 117
<212> TYPE: PRT
<213> ORGANISM: Artificial Sequence
<220> FEATURE:
<223> OTHER INFORMATION: hVH26

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: hVH27

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 57

```
<211> LENGTH: 117
<212> TYPE: PRT
<213> ORGANISM: Artificial Sequence
<220> FEATURE:
<223> OTHER INFORMATION: hVH28

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Gln Ala Tyr Gly His Tyr Met Asp Tyr Trp Gly Gln Gly Thr Ser
            100                 105                 110

Val Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: hVH29

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Leu
            100                 105                 110

Val Thr Val Ser Ser
        115

<210> SEQ ID NO 59
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 59

Gln Val Gln Leu Lys Gln
1               5
```

```
<210> SEQ ID NO 60
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 60

Asp Val Leu Met Thr Gln
1               5

<210> SEQ ID NO 61
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 61

Asp Ile Val Met Thr Gln
1               5

<210> SEQ ID NO 62
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 62

Asp Val Leu Met Thr Arg
1               5

<210> SEQ ID NO 63
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 63

Asp Ile Val Ile Thr Gln
1               5

<210> SEQ ID NO 64
<211> LENGTH: 6
<212> TYPE: PRT
<213> ORGANISM: Artificial Sequence
<220> FEATURE:
<223> OTHER INFORMATION: Variable light chain sequence variant

<400> SEQUENCE: 64

Asp Ile Val Leu Thr Gln
1               5

<210> SEQ ID NO 65
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 65

Gln Val Gln Leu Lys Glu
1               5
```

```
<210> SEQ ID NO 66
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 66

Glu Val Gln Leu Gln Gln
1               5

<210> SEQ ID NO 67
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 67

Gln Val Gln Leu Asn Gln
1               5

<210> SEQ ID NO 68
<211> LENGTH: 6
<212> TYPE: PRT
<213> ORGANISM: Artificial Sequence
<220> FEATURE:
<223> OTHER INFORMATION: Variable heavy chain sequence variant

<400> SEQUENCE: 68

Gln Val Gln Leu Thr Gln
1               5

<210> SEQ ID NO 69
<211> LENGTH: 112
<212> TYPE: PRT
<213> ORGANISM: Artificial Sequence
<220> FEATURE:
<223> OTHER INFORMATION: BT063 VL

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys Arg Ser Gln Asn Ile Val His Ser
            20                  25                  30

Asn Gly Asn Thr Tyr Leu Glu Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 70
<211> LENGTH: 117
<212> TYPE: PRT
<213> ORGANISM: Artificial Sequence
<220> FEATURE:
<223> OTHER INFORMATION: BT-063 VH

<400> SEQUENCE: 70
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ala Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Ser Ala Ala Phe Met
        50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Lys Gln Ala Tyr Gly His Tyr Met Asp Tyr Trp Gly Gln Gly Thr Ser
            100                 105                 110

Val Thr Val Ser Ser
        115

<210> SEQ ID NO 71
<211> LENGTH: 13
<212> TYPE: PRT
<213> ORGANISM: Artificial Sequence
<220> FEATURE:
<223> OTHER INFORMATION: BT-063 VL CDR1

<400> SEQUENCE: 71

Ser Ser Gln Asn Ile Val His Ser Asn Gly Asn Thr Tyr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: BT-063 VL CDR2

<400> SEQUENCE: 72

Lys Val Ser Asn Arg Phe Ser Gly Val Pro Asp Arg
1               5                   10

<210> SEQ ID NO 73
<211> LENGTH: 6
<212> TYPE: PRT
<213> ORGANISM: Artificial Sequence
<220> FEATURE:
<223> OTHER INFORMATION: BT-063 VL CDR3

<400> SEQUENCE: 73

Gly Ser His Val Pro Trp
1               5

<210> SEQ ID NO 74
<211> LENGTH: 10
<212> TYPE: PRT
<213> ORGANISM: Artificial Sequence
<220> FEATURE:
<223> OTHER INFORMATION: BT-063 VH CDR1

<400> SEQUENCE: 74

Ala Ser Gly Phe Ser Phe Ala Thr Tyr Gly
1               5                   10

<210> SEQ ID NO 75
<211> LENGTH: 16
```

```
-continued

<212> TYPE: PRT
<213> ORGANISM: Artificial Sequence
<220> FEATURE:
<223> OTHER INFORMATION: BT-063 VH CDR2

<400> SEQUENCE: 75

Ile Trp Arg Gly Gly Ser Thr Asp Tyr Ser Ala Ala Phe Met Ser Arg
1               5                   10                  15

<210> SEQ ID NO 76
<211> LENGTH: 8
<212> TYPE: PRT
<213> ORGANISM: Artificial Sequence
<220> FEATURE:
<223> OTHER INFORMATION: BT-063 VH CDR3

<400> SEQUENCE: 76

Gln Ala Tyr Gly His Tyr Met Asp
1               5
```